US012361542B2

(12) United States Patent
Braman et al.

(10) Patent No.: US 12,361,542 B2
(45) Date of Patent: Jul. 15, 2025

(54) SYSTEMS AND METHODS FOR DEEP ORTHOGONAL FUSION FOR MULTIMODAL PROGNOSTIC BIOMARKER DISCOVERY

(71) Applicant: TEMPUS AI, INC., Chicago, IL (US)

(72) Inventors: Nathaniel Braman, Cleveland, OH (US); Jagadish Venkataraman, Menlo Park, CA (US); Emery T. Goossens, Midvale, UT (US)

(73) Assignee: TEMPUS AI, INC., Chicago, IL (US)

( * ) Notice: Subject to any disclaimer, the term of this patent is extended or adjusted under 35 U.S.C. 154(b) by 482 days.

(21) Appl. No.: 17/686,131

(22) Filed: Mar. 3, 2022

(65) Prior Publication Data
US 2022/0292674 A1    Sep. 15, 2022

Related U.S. Application Data

(60) Provisional application No. 63/155,941, filed on Mar. 3, 2021.

(51) Int. Cl.
*G16H 30/20*    (2018.01)
*G06N 3/045*    (2023.01)
*G06T 7/00*    (2017.01)

(52) U.S. Cl.
CPC .......... *G06T 7/0012* (2013.01); *G06N 3/045* (2023.01); *G16H 30/20* (2018.01);
(Continued)

(58) Field of Classification Search
CPC ......... G06T 7/0012; G06T 2207/30024; G06T 2207/30004; G06T 2207/30096;
(Continued)

(56) References Cited

U.S. PATENT DOCUMENTS 10,395,772 B1    8/2019  Lucas et al.
10,902,952 B2    1/2021  Lucas et al.
(Continued)

FOREIGN PATENT DOCUMENTS

WO    2020/142563 A1    7/2020
WO    2021/081253 A1    4/2021
(Continued)

OTHER PUBLICATIONS

Lin et al. "Orthogonalization-guided feature fusion network for multimodal 2D+ 3D facial expression recognition." IEEE Transactions on Multimedia 23 (2020): 1581-1591 (Year: 2020).*
(Continued)

*Primary Examiner* — Sumati Lefkowitz
*Assistant Examiner* — Michael Adam Shariff
(74) *Attorney, Agent, or Firm* — MARSHALL, GERSTEIN & BORUN LLP

(57) ABSTRACT

A system and method are provided for identifying a multimodal biomarker of a prognostic prediction, using a deep learning framework trained to analyze different modality data, including radiomic image data, pathology image data, and molecular image data to obtain unimodal embedding predictions from those modality data and generate multimodal embedding predictions, through application of a loss minimization and attention-based fusion processes.

19 Claims, 12 Drawing Sheets

(52) U.S. Cl.
CPC ............... *G06T 2207/10116* (2013.01); *G06T 2207/20084* (2013.01); *G06T 2207/30024* (2013.01); *G06T 2207/30096* (2013.01)

(58) Field of Classification Search
CPC . G06T 2207/20084; G06T 2207/10081; G06T 2207/10088; G06T 2207/10116; G16H 30/00; G16H 30/20; G06V 2201/03; G06V 10/82; G06V 10/806; G06N 3/045; G06N 3/0455; G06N 3/0464; G06N 3/09; G06N 3/02
See application file for complete search history.

(56) References Cited

U.S. PATENT DOCUMENTS

| | | | |
|---|---|---|---|
| 10,957,041 | B2 | 3/2021 | Yip et al. |
| 10,975,445 | B2 | 4/2021 | Venkat et al. |
| 11,043,283 | B1 | 6/2021 | Bell et al. |
| 11,043,304 | B2 | 6/2021 | Lozac'hmeur et al. |
| 11,081,210 | B2 | 8/2021 | Perera |
| 11,145,416 | B1 | 10/2021 | Hafez et al. |
| 11,922,629 | B2 * | 3/2024 | Guida ............... A61B 5/055 |
| 2020/0075169 | A1 | 3/2020 | Lau et al. |
| 2020/0098448 | A1 | 3/2020 | Shah et al. |
| 2020/0118644 | A1 | 4/2020 | Khan et al. |
| 2020/0135303 | A1 | 4/2020 | Barber |
| 2020/0210852 | A1 | 7/2020 | Igartua et al. |
| 2020/0211716 | A1 | 7/2020 | Lefkofsky et al. |
| 2020/0258601 | A1 | 8/2020 | Lau |
| 2020/0335102 | A1 | 10/2020 | Lefkofsky et al. |
| 2020/0365232 | A1 | 11/2020 | Jaros et al. |
| 2020/0381087 | A1 | 12/2020 | Ozeran et al. |
| 2020/0395097 | A1 | 12/2020 | Chang et al. |
| 2021/0057042 | A1 | 2/2021 | Beaubier et al. |
| 2021/0057071 | A1 | 2/2021 | Barber et al. |
| 2021/0090694 | A1 | 3/2021 | Colley et al. |
| 2021/0098078 | A1 | 4/2021 | Lozac'hmeur et al. |
| 2021/0115511 | A1 | 4/2021 | Blidner |
| 2021/0118559 | A1 | 4/2021 | Lefkofsky |
| 2021/0151192 | A1 | 5/2021 | Lucas et al. |
| 2021/0155989 | A1 | 5/2021 | Salahudeen et al. |
| 2021/0172931 | A1 | 6/2021 | Larsen et al. |
| 2022/0367053 | A1 * | 11/2022 | Mahmood ............... G16B 40/20 |

FOREIGN PATENT DOCUMENTS

| | | | |
|---|---|---|---|
| WO | 2021/113821 | A1 | 6/2021 |
| WO | 2021/168143 | A1 | 8/2021 |

OTHER PUBLICATIONS

Singanamalli et al. "Supervised multi-view canonical correlation analysis: Fused multimodal prediction of disease diagnosis and prognosis"; Medical Imaging 2014: Biomedical Applications in Molecular, Structural, and Functional Imaging; vol. 9038. SPIE (Year: 2014).*

Lin et al. "Orthogonalization-guided feature fusion network for multimodal 2D+ 3D facial expression recognition." IEEE Transactions on Multimedia 23: 1581-1591 (Year: 2020).*

Braman et al., Deep orthogonal fusion: multimodal prognostic biomarker discovery integrating radiology, pathology, genomic and clinical data, 16th European Conference—Computer Vision—ECCV 2020, pp. 667-677 IN: de Bruijne et al. (eds.), MICCAI 2021, LNCS 12905 (Sep. 21, 2021).

* cited by examiner

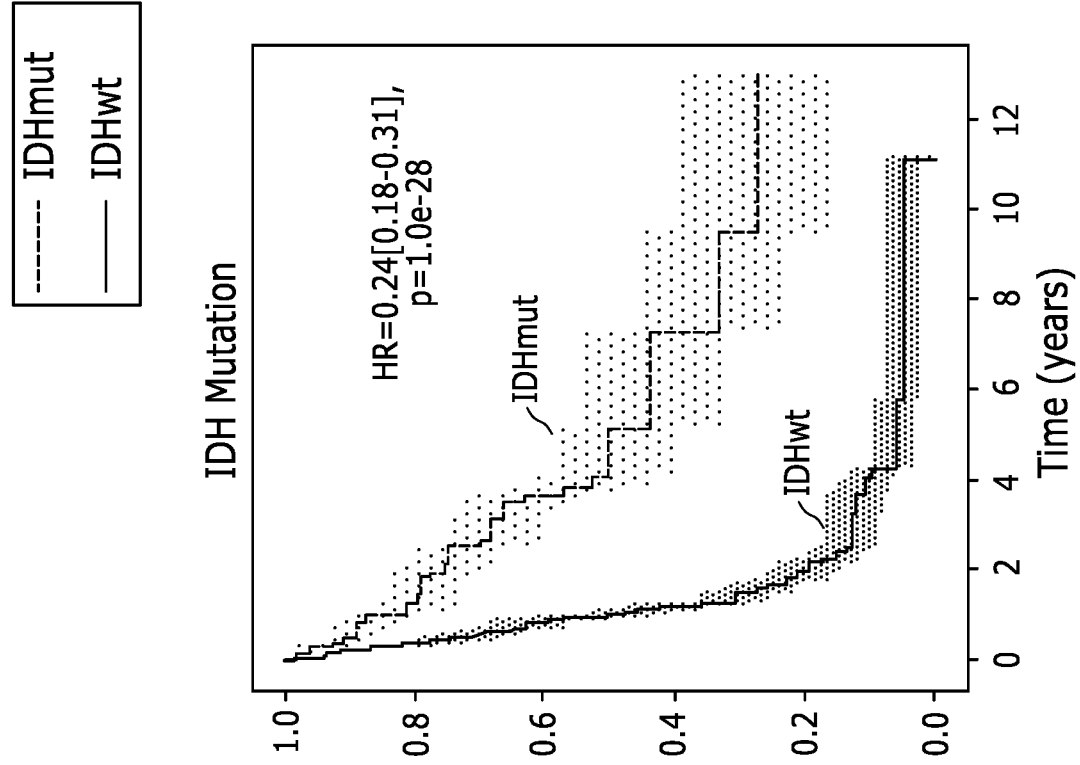
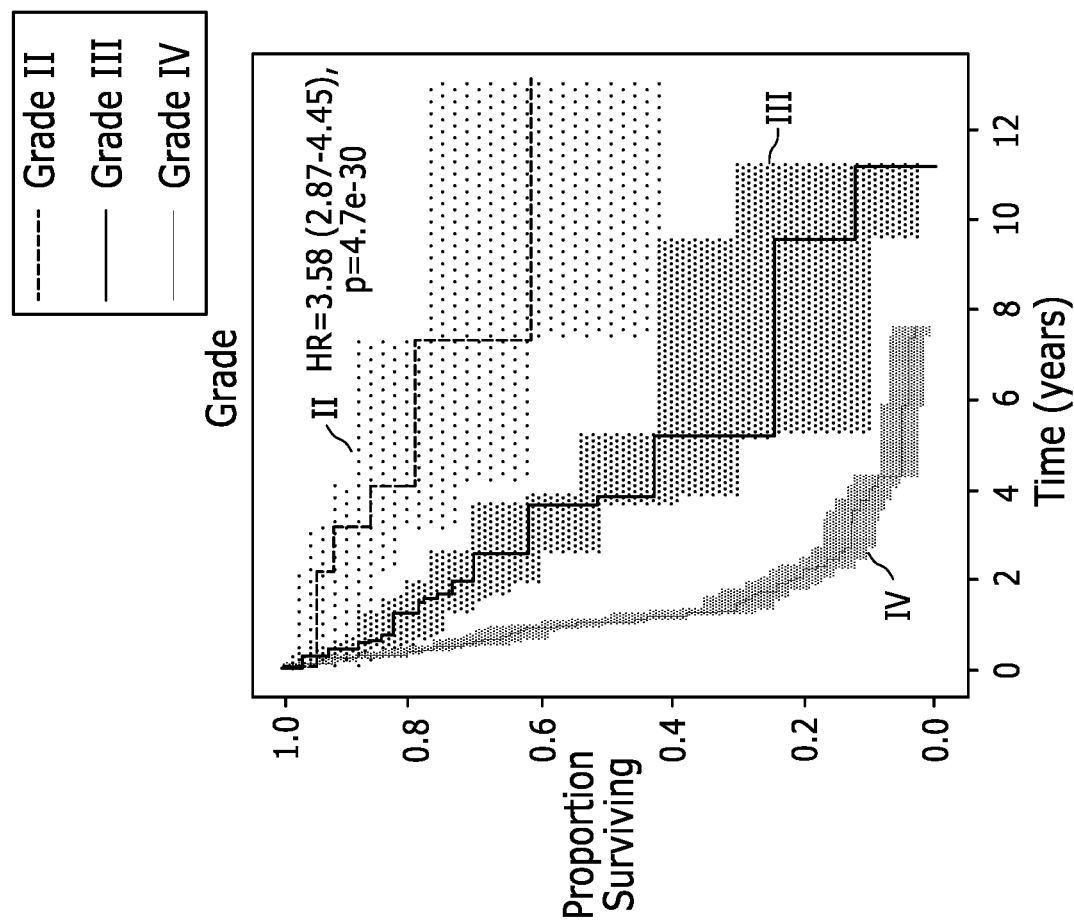
FIG. 7A
FIG. 7B

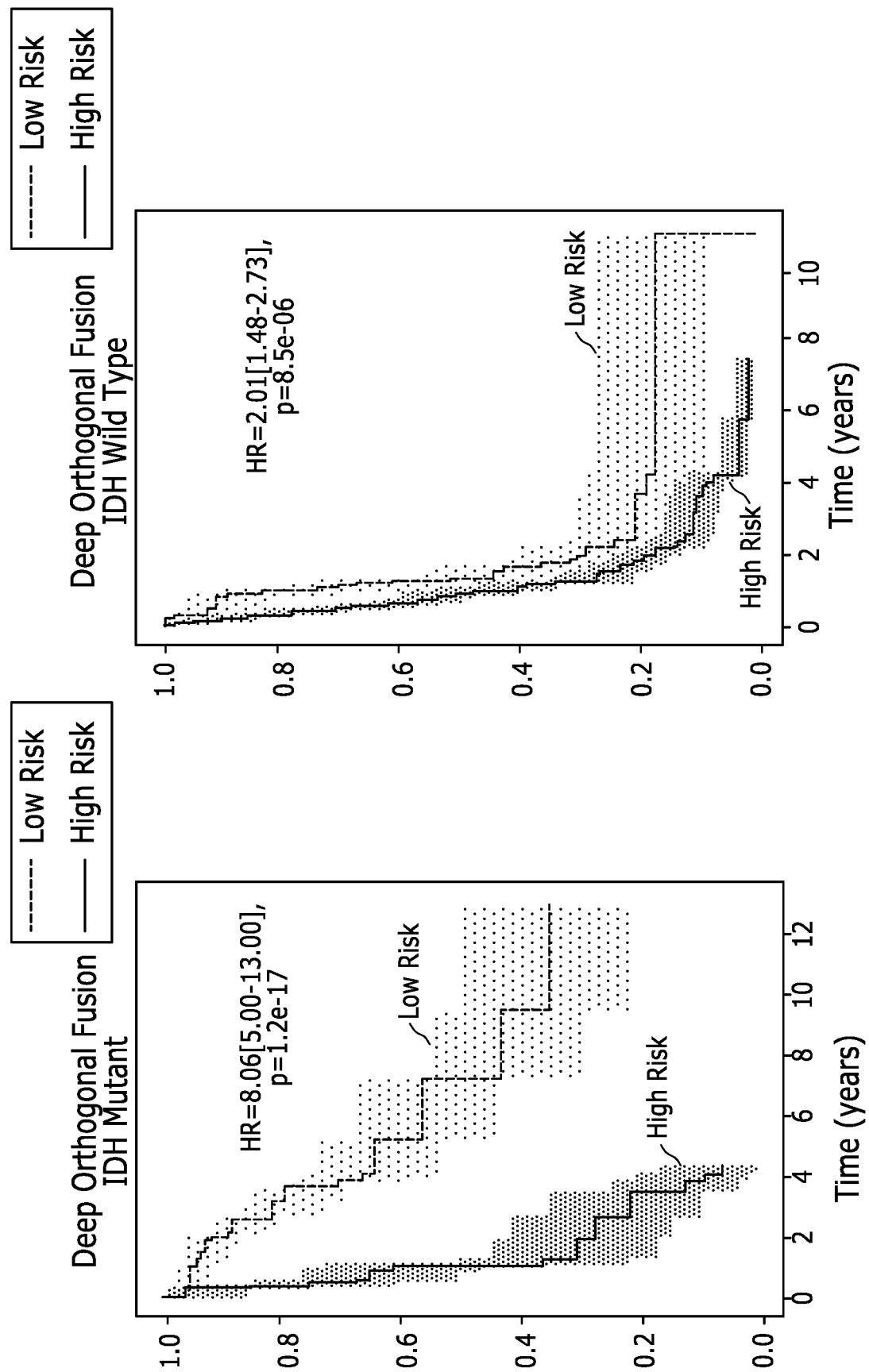

SYSTEMS AND METHODS FOR DEEP ORTHOGONAL FUSION FOR MULTIMODAL PROGNOSTIC BIOMARKER DISCOVERY

CROSS-REFERENCE TO RELATED APPLICATIONS

This application claims priority to U.S. Provisional Application No. 63/155,941, filed Mar. 3, 2021, which is incorporated herein by reference in its entirety.

FIELD OF THE INVENTION

The present disclosure relates to determining cancer-related biomarker(s) for predicting outcomes and, more particularly, determining multimodal biomarkers using deep orthogonal fusion.

BACKGROUND

The background description provided herein is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

Cancer diagnosis and treatment plans are driven by multiple streams of data, which are acquired from several modalities, such as radiology scans, molecular profiling, histology slides, and clinical variables. Each one characterizes tumor biology along a different dimension and collectively enables clinicians to optimize therapeutic approach and estimate patient prognosis. Advances in molecular profiling techniques have enabled omics data mining for multi-gene predictors, bringing precision medicine to the forefront of clinical practice. More recently, computational techniques in the field of radiology are also being investigated to identify imaging based-phenotypes of treatment response and patient survival. Such approaches leverage large sets of explicitly designed image features or entail the discovery of image patterns by optimizing the predictive performance of a highly parameterized deep learning model, such as a convolutional neural network (CNN). Along similar lines, the digitization of histopathology slides has opened new avenues for tissue-based assays that can stratify patients by risk from H&E slide images alone.

Despite showing some promise, these different modalities are implemented individually. There is a need to explore the complementary nature of these various modalities in a comprehensive clinical assessment. In particular, we believe there is a need provide a combinational approach in a quantitative, machine learning setting in the hopes of yielding a more confident prediction of patient outcomes than is currently achievable in isolated, unimodal analysis.

SUMMARY OF THE INVENTION

In accordance with an embodiment, a computer-implemented method for identifying a multimodal biomarker of a prognostic prediction for a tumor sample, the method comprises: obtaining, using one or more processors, a radiomic image modality dataset for a tumor sample; obtaining, using the one or more processors, a pathology image modality dataset for the tumor sample; obtaining, using the one or more processors, a molecular modality dataset for the tumor sample; providing, using the more or more processors, the radiomic image modality dataset, the pathology image modality dataset, and the molecular modality dataset to a trained deep learning framework and generating, using the trained deep learning framework, a radiomic embedding prediction, a pathology embedding prediction, and a molecular embedding prediction; and applying, using the trained deep learning framework, the radiomic embedding prediction, the pathology embedding prediction, and the molecular embedding prediction to a loss minimization and an embedding fusion to generate a multimodal embedding prediction as the multimodal biomarker for the tumor sample.

In accordance with an example, a computer-implemented method for identifying a multimodal biomarker of a prognostic prediction for a tumor sample, includes: obtaining, using one or more processors, a radiomic image modality dataset for a tumor sample; obtaining, using the one or more processors, a pathology image modality dataset for the tumor sample; obtaining, using the one or more processors, a molecular modality dataset for the tumor sample; providing, using the more or more processors, the radiomic image modality dataset, the pathology image modality dataset, and the molecular modality dataset to a trained deep learning framework and generating, using the trained deep learning framework, a radiomic embedding prediction, a pathology embedding prediction, and a molecular embedding prediction; and applying, using the trained deep learning framework, the radiomic embedding prediction, the pathology embedding prediction, and the molecular embedding prediction to a loss minimization and an embedding fusion to generate a multimodal embedding prediction as the multimodal biomarker for the tumor sample.

In accordance with another example, a system for identifying a multimodal biomarker of a prognostic prediction for a tumor sample, includes: one or more processors; and a trained deep learning framework application including computing instructions configured to be executed by the one or more processors to; receive a radiomic image modality dataset for a tumor sample, a pathology image modality dataset for the tumor sample, and a molecular modality dataset for the tumor sample; generate a radiomic embedding prediction, a pathology embedding prediction, and a molecular embedding prediction; and from the radiomic embedding prediction, the pathology embedding prediction, and the molecular embedding prediction, applying a loss minimization and an embedding fusion, generate a multimodal embedding prediction as the multimodal biomarker for the tumor sample.

In some examples, the radiomic image modality dataset is selected from the group consisting of a magnetic resonance imaging (MRI) image dataset, a computed (CT) image dataset, a fluorescence image dataset, and an x-ray image dataset.

In some examples, the pathology image modality dataset is selected from the group consisting of a hematoxylin and eosin (H&E) stained slide image dataset, an immunohistochemistry (IHC) stained slide image dataset, and a fluorescence in situ hybridization (FISH) image dataset.

In some examples, the molecular modality dataset is selected from the group consisting of gene sequencing data, RNA data, DNA data, methylation data, and proteomic data.

In some examples, the methods and/or trained deep learning framework includes generating the radiomic embedding prediction, the pathology embedding prediction, and the molecular embedding prediction includes: feeding, within the trained deep learning framework, the radiomic image modality dataset to a radiomic modality neural network trained to generate the radiomic embedding prediction; feeding, within the trained deep learning framework, the pathology image modality dataset to a pathology modality neural network trained to generate pathology embedding prediction; and feeding, within the trained deep learning framework, the molecular modality dataset to a molecular modality neural network trained to generate the molecular embedding prediction.

In some examples, the radiomic modality neural network is a convolution neural network. In some examples, the convolutional neural network has been trained using multi-parametric MRI training images and labeled image features. In some examples, the convolutional neural network comprises a T1 trained convolutional neural network branch, a T2 trained convolution neural network branch, and a labeled image features branch.

In some examples, the pathology modality neural network is a convolution neural network.

In some examples, the molecular modality neural network is a self-normalizing neural network.

In some examples, the trained deep learning framework includes a unimodal embeddings layer for generating the radiomic embedding prediction, the pathology embedding prediction, and the molecular embedding prediction and a fully-connected output layer for generating the multimodal embedding prediction.

In some examples, the trained deep learning framework is configured to apply a unimodal loss minimization for the unimodal embeddings layer.

In some examples, the trained deep learning framework is configured to apply a multimodal orthogonalization loss at the fully-connected output layer.

In some examples, the methods and/or trained deep learning frameworks further include: performing, using the trained deep learning framework, a multimodal fusion on the radiomic embedding prediction, the pathology embedding prediction, and the molecular embedding prediction; generating a multidimensional fusion matrix containing a plurality of multidimensional embeddings, containing at least one or more bi-modal embeddings or one or more tri-modal embeddings; and determining the multimodal embedding prediction from a comparison of plurality of multidimensional embeddings.

In some examples, the multimodal embedding prediction is a prediction of overall survival rate corresponding to the tumor sample.

In some examples, the multimodal embedding prediction is generated by: generating a plurality of multimodal embeddings each having a prediction score; and identifying a maximum prediction score as the multimodal embedding prediction.

In some examples, the methods further include, using the loss minimization, applying a multimodal orthogonalization across the radiomic embedding prediction, the pathology embedding prediction, and the molecular embedding prediction.

In some examples, the methods further include applying an attention weighting to the radiomic embedding prediction, the pathology embedding prediction, and the molecular embedding prediction and, in response, performing the embedding fusion to generate the multimodal embedding prediction.

In some examples, the methods further include: receiving additional features from the radiomic image modality dataset, the pathology image modality dataset, and/or the molecular modality dataset, the additional features not being used by the deep learning framework in generating the radiomic embedding prediction, the pathology embedding prediction, and the molecular embedding prediction; and using, in the trained deep learning framework, the additional features to generate the multimodal embedding prediction.

In some examples, the trained deep learning framework includes a radiomic modality neural network, a pathology modality neural network, and a molecular modality neural network. In some examples, the radiomic modality neural network, the pathology modality neural network, and the molecular modality neural network are contained in layers of a neural network. In some examples, the radiomic modality neural network, the pathology modality neural network, and the molecular modality neural network are separate neural networks sharing one or more fully-connected layers.

BRIEF DESCRIPTION OF THE DRAWINGS

The figures described below depict various aspects of the system and methods disclosed herein. It should be understood that each figure depicts an example of aspects of the present systems and methods.

FIGS. 7A-7B illustrate Kaplan Meier plots showing the stratification of patients by overall survival in risk groups derived from application of the system of FIGS. 1 and 2, in accordance with an example. FIG. 7A shows the stratification of glioma patients by grade; and FIG. 7B shows the IDH (Isocitrate dehydrogenase) mutation status.

FIGS. 8A-8D illustrate Kaplan Meier plots of an example application of the systems of FIGS. 1 and 2 showing risk group stratifies by overall survival into subsets according to their grade, Grade II/III (FIG. 8A) and Grade IV (FIG. 8B) and according to IDH status, IDH mutation (FIG. 8C) and IDH wild type (FIG. 8D), in accordance with an example.

DETAILED DESCRIPTION

Figure 1:
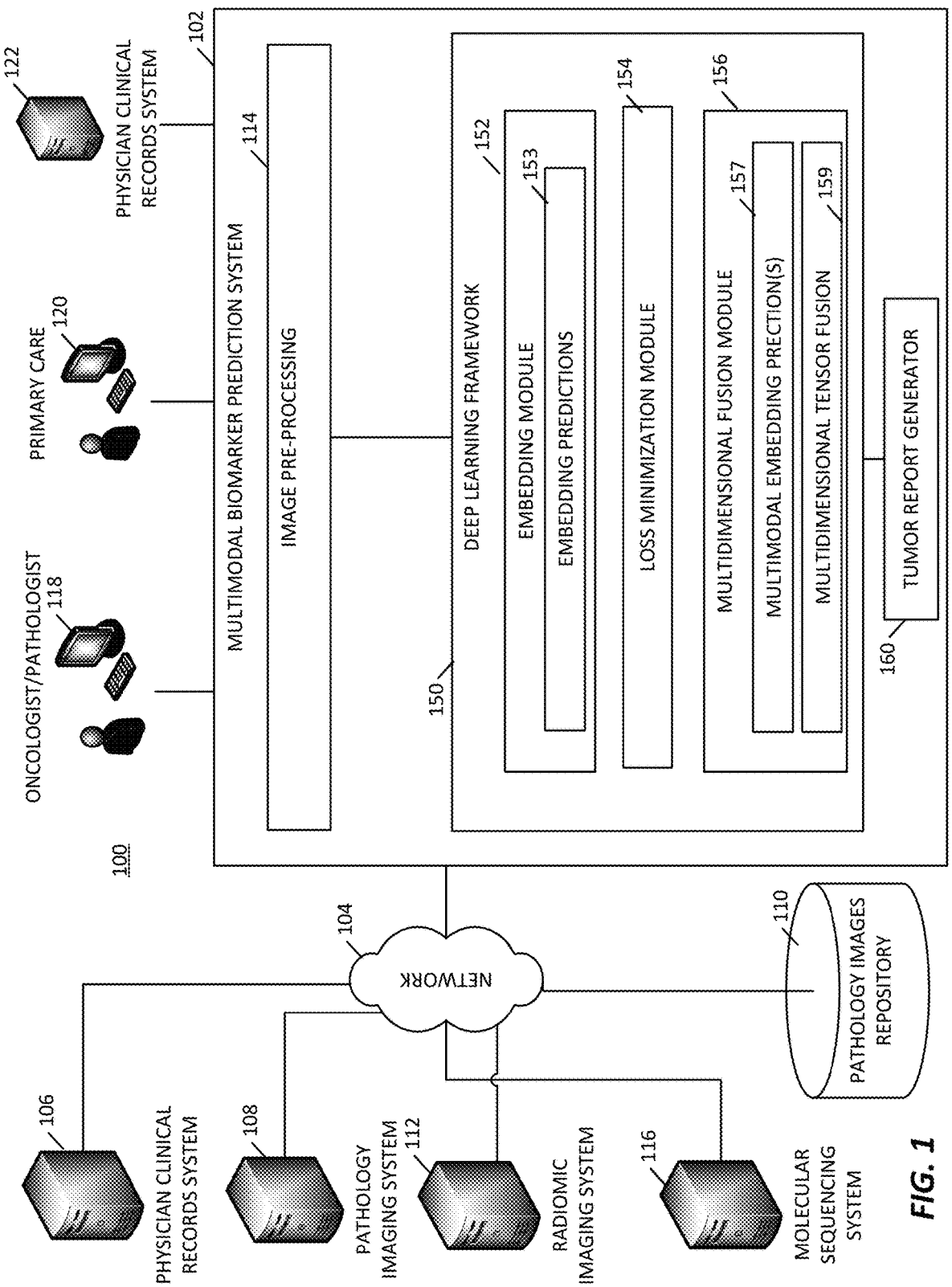
FIG. 1 illustrates a prediction system capable of analyzing multiple modality datasets for a sample and determining a multimodal biomarker at a prognostic prediction of a pathology state or condition, in accordance with an example.

In various embodiments, the systems and methods disclosed determining a multimodal biomarker indicating a prognostic prediction for a tumor sample, a prognostic prediction such as an overall patient survival likelihood. In various examples, systems and methods include obtaining datasets collected from a tumor sample across different data capture modalities. These data capture modalities may be image-based modalities, such as a radiomic image modality and/or a pathology image modality, and these data capture modalities may be molecule-based modalities, such as a molecular modality. In some examples, other data capture modalities may be used as well to provide datasets, including clinical modalities that provide clinical data on a patient/subject. The systems and methods herein may include providing different modality datasets to a trained deep learning framework and generating, using the trained deep learning framework, embedding predictions corresponding to each modality dataset. These embedding predictions may correspond to predictions of overall patient survival based on the data for of each data capture modality. The present techniques apply these embeddings to a deep fusion process of the trained deep learning framework, where that deep fusion process generates multimodal embedding predictions that are more accurate than the embedding predictions based on the individual modalities taken in isolation. For example, the trained deep learning framework may apply a loss minimization and embedding fusion process that generates multimodal embedding predictions, which can serve as a multidimensional biomarkers for the tumor sample.

Thus, in various examples, the present techniques include systems and methods of generating multidimensional biomarkers that are predictive of pathology outcomes, such as survival rates, by fusing predictions across different data capture modalities. The present techniques may be used, for example, to identify between different gliomas, subdividing their malignancy into histological grades II-IV, where the grades differ in morphology and molecular heterogeneity, which correspond to pathology outcomes such as treatment resistance and short-term recurrence. With the present techniques, as shown in example data discussed here, we can provide a quantitative analysis of glioma and its tumor habitat (or any other number cancer types) by combing medical image modality data with other modality data such as molecular image modality data and clinical modality data.

The systems and methods herein are able to provide considerable advantageous over conventional systems. For example, some have proposed techniques that integrate genomics data with pathology analysis via a convolution neural network (CNN) and graph convolutional neural networks (GCN) for improved prognosis predictions in glioma patients. And some have integrated histology, clinical, and sequencing data by condensing each to a correlated prognostic feature representation. Others have introduced late-stage fusion approaches that incorporate feature-based representations from radiology with pathology features or genomic data to predict tumor recurrence. However, no conventional techniques combine different modality datasets (e.g., radiology, pathology, and genomic data) within a single deep learning framework for outcome prediction. Further, no conventional techniques deploy loss minimization and multidimensional fusion processes for improved outcome predictions.

Definitions

As used herein references to a "radiomic image modality dataset" refers to data derived from radiographic images and may include the radiomic images themselves. Example radiomic images include medical images captured by radiation-based image capture techniques, including but not limited to magnetic resonance imaging (MRI) images, a computed tomography (CT) images, positron emission tomography (PET) images, fluorescence images, and X-ray images. A "radiomic image modality dataset" may include, for example, raw radiomic images, compressed radiomic images, pixel-level data, data identifying different tissue, artifacts, etc. within image data, segmentation data, and metadata. Further, "radiomic image modality datasets" may be data resulting from trained machine learning models, such as models trained to identify cells, tissues, molecules, and/or artifacts in radiomic images.

As used herein references to a "pathology image modality dataset" refers to data derived from pathology images, where the derived data may include the pathology images themselves. Example pathology images include medical images captured from tissue samples taken from a subject, including images of stained pathology slides. Example pathology images include images of a hematoxylin and eosin (H&E) stained slides and an immunohistochemistry (IHC) stained slides, and fluorescence in situ hybridization (FISH) images. A "pathology image modality dataset" may include, for example, raw pathology images, compressed pathology images, pixel-level data, data identifying different tissue, artifacts, etc. within the image data, segmentation data, and metadata. Data derived from pathology images may include data derived from analysis of slides for H&E staining or IHC staining such as tumor infiltration, programmed death-ligand 1 (PD-L1) status, human leukocyte antigen (HLA) status, or other immunology-related features. The pathology image modality dataset may include features such as tumor mutation burden (TMB), ploidy, purity, nuclear-cytoplasmic ratio, large nuclei, cell state alterations, biological pathway activations, hormone receptor alterations, immune cell infiltration, immune biomarkers of MMR, MSI, PDL1, CD3, FOXP3, HRD, PTEN, PIK3CA; collagen or stroma composition, appearance, density, or characteristics; tumor budding, size, aggressiveness, metastasis, immune state, chromatin morphology; and other characteristics of cells, tissues, or tumors for prognostic predictions. Further, "pathology image modality datasets" may be data resulting from trained machine learning models, such as models trained to identify cells, tissues, molecules, and/or artifacts in pathology images.

As used herein references to a "molecular modality dataset" refers to data derived from sequencing reads of a tissue sample, where the derived data may include the sequencing reads themselves. Examples of molecular modality datasets include genomic data, including, for example, gene sequencing data, RNA data, DNA data, methylation data, and proteomic data. The sequencing reads may include next-generation sequencing (NGS) and may be long-read, short-read, or other forms of sequencing a patient's somatic and/or normal genome. Data derived from DNA and RNA sequencing may include genetic variants, which can be identified in a sequenced sample. The data may include data derived from genetic variants such as identifying single or multiple nucleotide polymorphisms, identifying whether a variation is an insertion or deletion event, identifying loss or gain of function, identifying fusions, calculating copy number variation, calculating microsatellite instability, calculating tumor mutational burden, or other structural variations within the DNA and RNA. The molecular dataset may include germline/somatic DNA-derived information of a patient and/or a patient's tumor. The molecular dataset may contain derived features, which may include raw sequencing results, such as those stored in FASTQ, BAM, VCF, or other sequencing file types known in the art, genes, mutations, variant calls, and variant characterizations. Genomic information from a patient's normal sample may be stored as germline and genomic information from a patient's tumor sample may be stored as somatic. Such molecular data may comprise a feature collection associated with the RNA-derived information of a patient, such as transcriptome information. These features may include, for example, raw sequencing results, transcriptome expressions, genes, mutations, variant calls, and variant characterizations. Features may also include normalized sequencing results, such as those normalized by transcripts per million (TMP). In examples, "molecular modality datasets" may be data resulting from trained machine learning models trained to identify features within molecular data, such as within genomic sequencing data.

As used herein references to a "Clinical modality dataset" refers to data associated with a patient, such as diagnosis, treatment history, age, gender and other information derived from the patient's demographic and clinical data. Examples of clinical modality datasets include unique patient specific data and/or collective patient data. Clinical modality datasets may include data collected from patient health records, such as clinical information based upon fields which have been entered into an electronic medical record (EMR) or an electronic health record (EHR). The clinical data may include features derived from structured, curated, and/or electronic medical or health records and may include clinical features such as diagnosis, symptoms, therapies, outcomes, patient demographics such as patient name, date of birth, gender, ethnicity, date of death, address, smoking status, diagnosis dates for cancer, illness, disease, diabetes, depression, other physical or mental maladies, personal medical history, family medical history, clinical diagnoses such as date of initial diagnosis, date of metastatic diagnosis, cancer staging, tumor characterization, tissue of origin, treatments and outcomes such as line of therapy, therapy groups, clinical trials, medications prescribed or taken, surgeries, radiotherapy, imaging, adverse effects, associated outcomes, genetic testing and laboratory information such as performance scores, lab tests, pathology results, prognostic indicators, date of genetic testing, testing provider used, testing method used, such as genetic sequencing method or gene panel, gene results, such as included genes, variants, expression levels/statuses, or corresponding dates associated with any of the above. Other clinical information may curated clinical information that has been generated from other sources, such as, from other modalities like from genetic sequencing reports or from medical image data. A clinical modality dataset may include a comprehensive collection of data across varying fields of medicine which may include diagnoses, responses to treatment regimens, genetic profiles, clinical and phenotypic characteristics, and/or other medical, geographic, demographic, clinical, or genetic features. In some examples, the clinical modality dataset includes feature collection associated with information derived from clinical records of a patient, which can include records from family members of the patient. These may be abstracted from unstructured clinical documents, EMR, EHR, or other sources of patient history. Such clinical data may include patient symptoms, diagnosis, treatments, medications, therapies, hospice, responses to treatments, laboratory testing results, medical history, geographic locations of each, demographics, or other features of the patient which may be found in the patient's medical record. Data about treatments, medications, therapies, and the like may be ingested as a recommendation or prescription and/or as a confirmation that such treatments, medications, therapies, and the like were administered or taken. The clinical modality dataset may include data pertaining to epigenomic features, such as, e.g., features collection associated with information derived from DNA modifications which are not changes to the DNA sequence and regulate the gene expression. These modifications can be a result of environmental factors based on what the patient may breathe, eat, or drink. These features may include DNA methylation, histone modification, or other factors which deactivate a gene or cause alterations to gene function without altering the sequence of nucleotides in the gene. The clinical modality dataset may include data pertaining to microbiome features, such as, e.g., features associated with information derived from the viruses and bacteria of a patient. These features may include viral infections which may affect treatment and diagnosis of certain illnesses as well as the bacteria present in the patient's gastrointestinal tract which may affect the efficacy of medicines ingested by the patient. The clinical modality dataset may include data pertaining to proteomic features, such as, e.g., features associated with information derived from the proteins produced in the patient. These features may include protein composition, structure, and activity; when and where proteins are expressed; rates of protein production, degradation, and steady-state abundance; how proteins are modified, for example, post-translational modifications such as phosphorylation; the movement of proteins between subcellular compartments; the involvement of proteins in metabolic pathways; how proteins interact with one another; or modifications to the protein after translation from the RNA such as phosphorylation, ubiquitination, methylation, acetylation, glycosylation, oxidation, or nitrosylation. In examples, "clinical modality datasets" may be data resulting from trained machine learning models trained to identify features within clinical data.

Additionally, an "Omics modality dataset" obtained from Omics module(s) (not shown) may also be included in the techniques herein and include data such as a feature collection (which is a collection of status characteristics) associated with all the different field of omics, including: cognitive genomics, a collection of features comprising the study of the changes in cognitive processes associated with genetic profiles; comparative genomics, a collection of features comprising the study of the relationship of genome structure and function across different biological species or strains; functional genomics, a collection of features comprising the study of gene and protein functions and interactions including transcriptomics; interactomics, a collection of features comprising the study relating to large-scale analyses of gene-gene, protein-protein, or protein-ligand interactions; metagenomics, a collection of features comprising the study of metagenomes such as genetic material recovered directly from environmental samples; neurogenomics, a collection of features comprising the study of genetic influences on the development and function of the nervous system; pangenomics, a collection of features comprising the study of the entire collection of gene families found within a given species; personal genomics, a collection of features comprising the study of genomics concerned with the sequencing and analysis of the genome of an individual such that once the genotypes are known, the individual's genotype can be compared with the published literature to determine likelihood of trait expression and disease risk to enhance personalized medicine suggestions; epigenomics, a collection of features comprising the study of supporting the structure of genome, including protein and RNA binders, alternative DNA structures, and chemical modifications on DNA; nucleomics, a collection of features comprising the study of the complete set of genomic components which form the cell nucleus as a complex, dynamic biological system; lipidomics, a collection of features comprising the study of cellular lipids, including the modifications made to any particular set of lipids produced by a patient; proteomics, a collection of features comprising the study of proteins, including the modifications made to any particular set of proteins produced by a patient; immunoproteomics, a collection of features comprising the study of large sets of proteins involved in the immune response; nutriproteomics, a collection of features comprising the study of identifying molecular targets of nutritive and non-nutritive components of the diet including the use of proteomics mass spectrometry data for protein expression studies; proteogenomics, a collection of features comprising the study of biological research at the intersection of proteomics and genomics including data which identifies gene annotations; structural genomics, a collection of features comprising the study of 3-dimensional structure of every protein encoded by a given genome using a combination of modeling approaches; glycomics, a collection of features comprising the study of sugars and carbohydrates and their effects in the patient; foodomics, a collection of features comprising the study of the intersection between the food and nutrition domains through the application and integration of technologies to improve consumer's well-being, health, and knowledge; transcriptomics, a collection of features comprising the study of RNA molecules, including mRNA, rRNA, tRNA, and other non-coding RNA, produced in cells; metabolomics, a collection of features comprising the study of chemical processes involving metabolites, or unique chemical fingerprints that specific cellular processes leave behind, and their small-molecule metabolite profiles; metabonomics, a collection of features comprising the study of the quantitative measurement of the dynamic multiparametric metabolic response of cells to pathophysiological stimuli or genetic modification; nutrigenetics, a collection of features comprising the study of genetic variations on the interaction between diet and health with implications to susceptible subgroups; cognitive genomics, a collection of features comprising the study of the changes in cognitive processes associated with genetic profiles; pharmacogenomics, a collection of features comprising the study of the effect of the sum of variations within the human genome on drugs; pharmacomicrobiomics, a collection of features comprising the study of the effect of variations within the human microbiome on drugs; toxicogenomics, a collection of features comprising the study of gene and protein activity within particular cell or tissue of an organism in response to toxic substances; mitointeractome, a collection of features comprising the study of the process by which the mitochondria proteins interact; psychogenomics, a collection of features comprising the study of the process of applying the powerful tools of genomics and proteomics to achieve a better understanding of the biological substrates of normal behavior and of diseases of the brain that manifest themselves as behavioral abnormalities, including applying psychogenomics to the study of drug addiction to develop more effective treatments for these disorders as well as objective diagnostic tools, preventive measures, and cures; stem cell genomics, a collection of features comprising the study of stem cell biology to establish stem cells as a model system for understanding human biology and disease states; connectomics, a collection of features comprising the study of the neural connections in the brain; microbiomics, a collection of features comprising the study of the genomes of the communities of microorganisms that live in the digestive tract; cellomics, a collection of features comprising the study of the quantitative cell analysis and study using bioimaging methods and bioinformatics; tomomics, a collection of features comprising the study of tomography and omics methods to understand tissue or cell biochemistry at high spatial resolution from imaging mass spectrometry data; ethomics, a collection of features comprising the study of high-throughput machine measurement of patient behavior; and videomics, a collection of features comprising the study of a video analysis paradigm inspired by genomics principles, where a continuous digital image sequence, or a video, can be interpreted as the capture of a single image evolving through time of mutations revealing patient insights.

In some embodiments, a robust collection of the example features, provided for each modality, may include all of the features disclosed for that modality or may include features across different modalities. However, the different modality datasets may include data on machine learning (and/or other) models optimized and/or trained from a selection of fewer features than in the exhaustive feature set. Such a constrained feature set may include, in some embodiments, from tens to hundreds of features in each modality dataset. As described further below, for each of the modality datasets, the present techniques may reduce the dataset to a lower dimensional space, to generate respective embeddings for each dataset, where these embeddings may be embedding predictions of prognosis for a subject. For example, an embedding prediction may include predicting the likelihood a patient's tumor may metastasize to the brain or the embedding prediction may be a prediction of overall patient survival. A machine learning model's constrained feature set may include the genomic results of a sequencing of the patient's tumor, derivative features based upon the genomic results, the patient's tumor origin, the patient's age at diagnosis, the patient's gender and race, and symptoms that the patient brought to their physicians attention during a routine checkup.

As used herein "embedding" refers to generating, capturing, or otherwise obtaining the underlying data distribution in a lower dimensional space from that of an input data source. In some examples, embeddings to a mapping of a discrete, e.g., categorical, variable to a vector of continuous numbers. For example, embeddings may include be a lower dimensional vector representing discrete variables.

Example Prediction System

FIG. 1 illustrates a prediction system 100 capable of analyzing multiple, different modality datasets and determining a multimodal biomarker of a prognostic prediction of a pathology state or condition for a subject. The system 100 includes a multimodal biomarker prediction system 102 that implements, among other things, data processing operations, trained deep learning framework operations, and report generating operations to analyze different modality datasets of a tissue sample and to predict the presence of a multimodal biomarker corresponding to the tissue samples.

Figure 10:
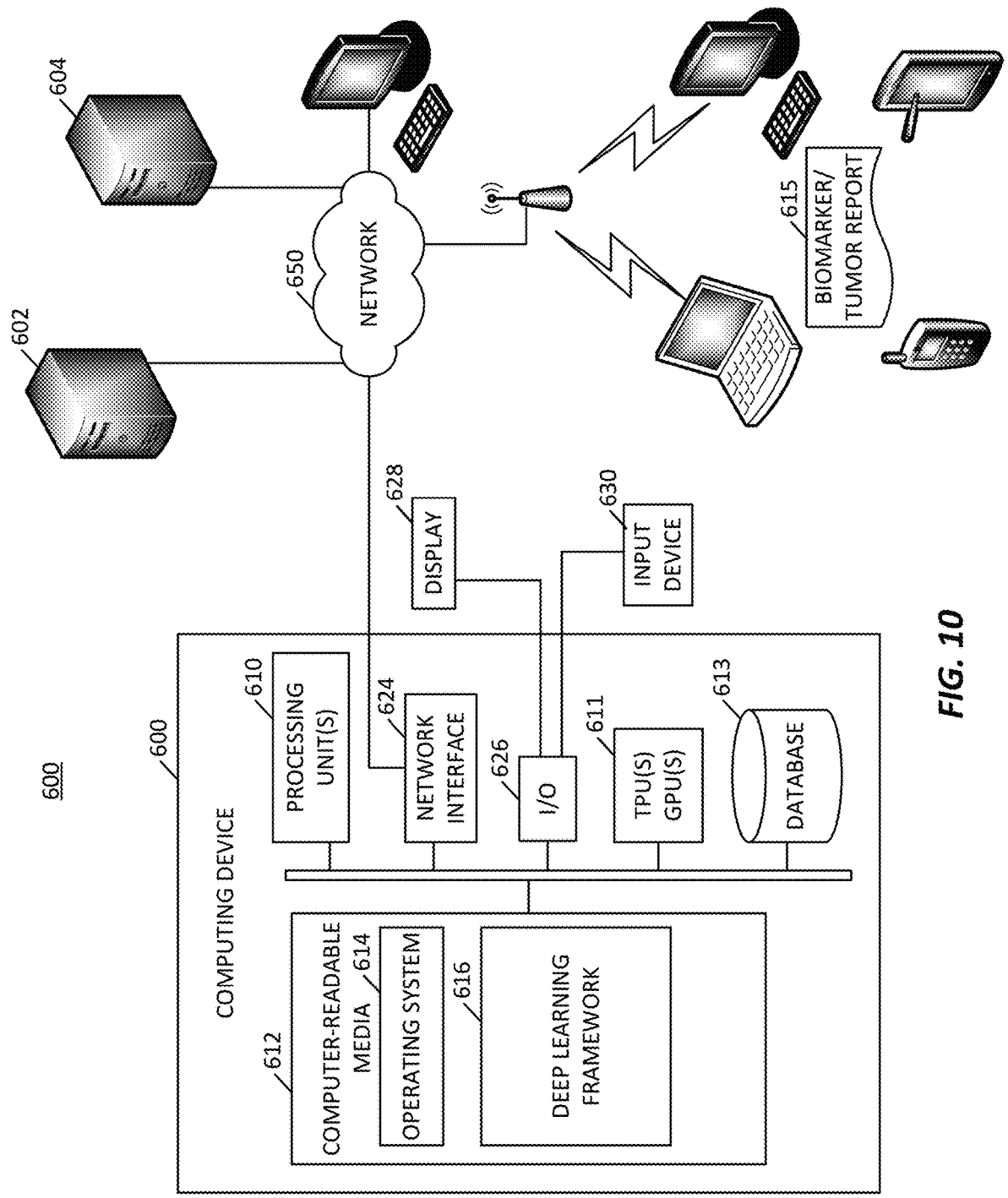
FIG. 10 illustrates an example computing device for implementing the prediction system of FIGS. 1 and 2 and other systems herein, in accordance with an example.

The multimodal biomarker prediction system 102 may be implemented on one or more computing devices, such as a computer, tablet or other mobile computing device, or server, such as a cloud server. The multimodal biomarker prediction system 102 may include a number of processors, controllers or other electronic components for processing or facilitating image capture, generation, or storage and image analysis, and deep learning tools for analysis of images, as described herein. An example computing device 600 for implementing the multimodal biomarker prediction system 102 is illustrated in FIG. 10.

As illustrated in FIG. 1, the multimodal biomarker prediction system 102 is connected to one or more medical data sources through a network 104. The network 104 may be a public network such as the Internet, private network such as a research institution's or corporation's private network, or any combination thereof. Networks can include, local area network (LAN), wide area network (WAN), cellular, satellite, or other network infrastructure, whether wireless or wired. The network 104 can be part of a cloud-based platform. The network 104 can utilize communications protocols, including packet-based and/or datagram-based protocols such as internet protocol (IP), transmission control protocol (TCP), user datagram protocol (UDP), or other types of protocols. Moreover, the network 104 can include a number of devices that facilitate network communications and/or form a hardware basis for the networks, such as switches, routers, gateways, access points (such as a wireless access point as shown), firewalls, base stations, repeaters, backbone devices, etc.

Via the network 104, the multimodal biomarker prediction system 102 is communicatively coupled to receive different modality datasets captured by different sources. These different modality datasets may be taken from the same tissue sample or from different tissue samples from the same subject. In some examples, these different modality datasets may be taken from different tissue samples and/or from different tissue samples across of a population of subjects, for example during training of a deep learning framework.

These data sources may include a clinical records systems 106 communicating clinical modality datasets, a pathology imaging system 108 capturing and communicating pathology image modality datasets, and an image repository 110 of stored pathology images. Any number of pathology image data sources may be communicatively coupled to the multimodal biomarker prediction system 102. The pathology images may be images captured by any dedicated digital pathology image scanners, e.g., any suitable optical histopathology slide scanner including 10×, 20×, and/or 40× resolution magnification scanners. In some examples, the pathology image modality datasets communicated from the sources 108 and 110 may include any one or more of hematoxylin and eosin (H&E) stained slide image datasets, immunohistochemistry (IHC) stained slide image datasets, and fluorescence in situ hybridization (FISH) image datasets.

In the illustrated example, the image sources 108 and 110 may communicate in the modality image dataset image data, genomic data, patient data, treatment data, historical data, etc., in accordance with the techniques and processes described herein. Each of the image sources 108 and 110 may represent multiple pathology image sources. Further, each of these pathology image sources may be considered a different data source, those data sources capable of generating and providing imaging data that differs from other providers, hospitals, etc. The pathology image modality datasets from each may differ in one or more ways, resulting from different data source-specific bias, such as in different dyes, biospecimen fixations, embeddings, staining protocols, and distinct pathology imaging instruments and settings.

Further still, the multimodal biomarker prediction system 102 may receive radiomic image modality datasets from one or more radiomic imaging systems 112. The radiomic imaging systems 112 may include one or more magnetic resonance imaging (MRI) systems, computed tomography (CT) imaging systems, fluorescence in situ hybridization (FISH) imaging systems, or other sources of radiology based images. Thus in some examples, the radiomic image modality datasets may include one or more of a magnetic resonance imaging (MRI) image dataset, a computed (CT) image dataset, a fluorescence image dataset, and an x-ray image dataset.

In some examples, including that illustrated in FIG. 1, the multimodal biomarker prediction system 102 includes an image pre-processing sub-system 114 that performs initial image processing to enhance image modality datasets for faster processing in training a deep learning framework and for performing multimodal biomarker prediction using a trained deep learning framework. Such image pre-processing may include performing a normalization process on received image data, including one or more of color normalization, intensity normalization, and imaging source normalization, to compensate for and correct for differences in the received image data. While in some examples the multimodal biomarker prediction system 102 receives radiomic and pathology image modality datasets, in other example implementations the sub-system 114 may generate one or more image modality datasets. For example, the sub-system 114 may be configured to receive pathology images and generate composite images (e.g., composite pathology images) by aligning shifted images to compensate for vertical/horizontal shift. In any event, the image pre-processing of sub-system 114 allows a trained deep learning framework to more efficiently analyze images across large data sets (e.g., over hundreds, thousands, or millions of medical images), thereby resulting in faster training and faster analysis processing.

The image pre-processing sub-system 114 may perform further image processing that removes artifacts and other noise from received radiomic image datasets and pathology image datasets, e.g., by performing a mask processing and tissue detection, for example, to identify regions of the images corresponding to tissue for subsequent analysis, classification, and segmentation. For example, the radiomic and pathology image datasets may be analyzed on a tile-basis, receiving the image datasets at a first image resolution, downsampling them to a second image resolution, and then performing a normalization on the downsampled image datasets, such as color and/or intensity normalization, and removing non-tissue objects from the image datasets, and then apply a tile mask to generate tiles representing subsections of the received radiomic and pathology image datasets.

Further still, the multimodal biomarker prediction system 102 may receive molecular modality datasets from one or more molecular sequencing system 116, such as a next generation sequencer (NGS). For example, the molecular sequencing system 116 may communicate molecular modality datasets in the form of gene sequencing data, RNA data, DNA data, methylation data, proteomic data, or any other similar molecular analysis derived from tissue samples.

The multimodal biomarker prediction system 102 may be a standalone system interfacing with the external (e.g., third party) network-accessible systems 106, 108, 110, 112, and 116. In some examples, the multimodal biomarker prediction system 102 may be integrated with one or more of these systems, including as part of a distributed cloud-based platform. For example, the system 102 may be integrated with a pathology imaging system, such as a digital H&E stain imaging system, e.g. to allow for expedited biomarker analysis and reporting at the imaging station. Indeed, any of the functions described in the techniques herein may be distributed across one or more network accessible devices, including cloud-based devices.

In some examples, the multimodal biomarker prediction system 102 is part of a comprehensive multimodal biomarker prediction, patient diagnosis, and patient treatment system. For example, the multimodal biomarker prediction system 102 may be coupled to communicate predicted multimodal biomarker information, tumor prediction, and tumor state information to external systems, including to a computer-based pathology lab/oncology system 118 that may receive a generated multimodal biomarker report including image overlay mapping and use the same for further diagnosing cancer state of the patient and for identifying matching therapies for use in treating the patient. The multimodal biomarker prediction system 102 may further send generated reports to a computer system 120 of the patient's primary care provider and to a physician clinical records system 122 for databasing the patients report with previously generated reports on the patient and/or with databases of generated reports on other patients for use in future patient analyses, including deep learning analyses, such as those described herein.

The multimodal biomarker prediction system 102 includes a deep learning framework 150 trained to analyze the different modality datasets and generate a multimodal biomarker predicting a prognostic prediction of a pathology state or condition for a subject. In some examples, the deep learning framework 150 is configured to implement various machine learning algorithms to analyze each or some subset of the different modality datasets. More particularly, in various examples, the deep learning framework 150 is configured and trained to receive radiomic image modality datasets, a pathology image modality datasets, and a molecular modality datasets, or any number of further modality datasets and generate embedding predictions corresponding to each modality dataset, (termed "unimodal embedding predictions"). These unimodal embedding predictions may correspond to predictions of the state or condition of a subject or survival rates of a subject, for example a patient may be identified as eligible for surgery, treatments, or other diagnostic or prognostic outcomes. The deep learning framework 150 may be configured and trained to determine, from these unimodal embeddings, a multimodal embedding predictions that serves as a multimodal biomarker for the tumor sample, providing a more robust prediction based on a combination of different modality datasets and different predictions.

In the illustrated example, a radiomic image modality dataset from the system 112, the pathology image modality dataset from the system 108, and a molecular modality dataset from the systems 116 are communicated to the trained deep learning framework 150 that includes an embedding module 152, a loss minimization module 154, and a fusion module 156. In some examples, the embedding module 152 includes trained machine learning algorithms that generate unimodal embedding predictions 153 for each of the received modality datasets. For example, the embedding module 152 may generate radiomic embedding predictions, pathology embedding predictions, molecular embedding prediction, and clinical embedding predictions. More generally, the embedding module 152 may be configured to deploy any suitable algorithms, rule sets, analysis methods, or techniques capable of receiving datasets at a higher dimensional space and generating an underlying data distribution in a lower dimensional space, whether stored as a vector mapping, continuous numerical expression, or in another lower dimensional format.

In some examples, the loss minimization module 154 includes one or more minimization algorithms configured to receive and optimize the embedding predictions 153 by removing highly correlated embedding predictions, redundant embedding predictions, biases, and other outliers affecting the variance of the model inputs to allow for a reduced set of embedding predictions with a higher correlation to predictive outcomes. In some examples, the loss minimization module 154 employs an orthogonalization loss function, e.g., a Multimodal Orthogonalization (MMO) loss function that penalizes the correlation between unimodal embeddings and encourages each unimodal representation to provide independent prognostic information.

In some examples, the multidimensional fusion module 156 includes trained machine learning algorithms and generates multimodal embedding predictions 157 from the unimodal embedding predictions 153 and the applied loss minimization algorithms of module 154. In some examples, the multidimensional fusion module 156 generates a number of multimodal embedding predictions and then applies a selection rule to identify one or a subset thereof as the multimodal embedding prediction for the received datasets. In some examples, the multidimensional fusion module 156 generates a multidimensional tensor fusion 159 of combinational relationships between embedding predictions. For example, the multidimensional fusion module 156 may apply an attention-gated tensor fusion product to generate the tensor fusion 159 that includes all possible interactions between each dataset modality. In some examples, tensor fusion 159 comprises unimodal embedding predictions, bi-modal embedding predictions representing two connected embedding predictions, tri-modal embedding predictions representing three connected embedding predictions, or higher ordered embedding predictions.

The multimodal biomarker prediction system 102 further includes a prediction report generator 160, which may be configured to receive the multimodal embedding predictions 157 and/or tensor fusion data 159 and generate a diagnostic prediction report, e.g., a displayable report that is communicated to or made accessible to the pathology lab 118, the primary care physician system 120, the physician clinical records systems 122, or any of the modality data sources 106, 108, 110, 112, or 116.

Figure 2:
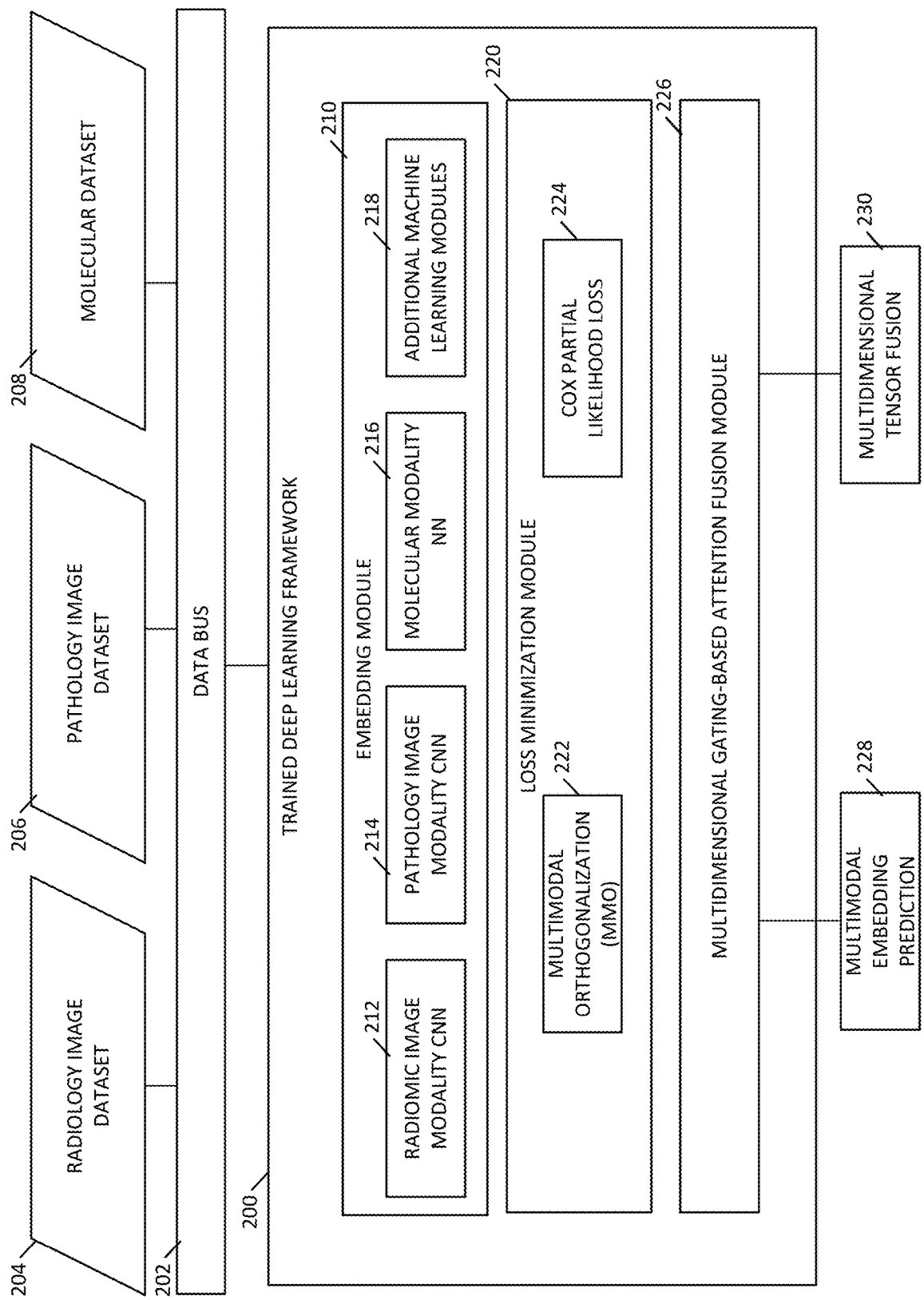
FIG. 2 illustrates a trained deep learning framework for generating the multimodal biomarkers as may be employed in the prediction system of FIG. 1 and having an embedding module, loss minimization module, and fusion module, in accordance with an example.

FIG. 2 illustrates a trained deep learning framework 200 that may be an example implementation of the framework 150. In the illustrated example, three different modality datasets are provided to the deep learning framework 200 through a data bus 202: a radiomic image modality dataset 204, a pathology image modality dataset 206, and a molecular modality dataset 208. The deep learning framework 200 includes an embedding module 210 configured with separate trained machine learning algorithms for each modality dataset. In the illustrated example, the embedding module 210 includes a radiomic image modality convolutional neural network (CNN) 212 and a pathology image modality CNN 214, each trained to generate one or more embeddings from the received dataset sets 204 and 206, respectively. The embedding module 210 further includes molecular modality neural network (NN) 216 trained to generate one or more embeddings from the received molecular dataset 208. In some examples, the molecular modality NN 216 is a self-normalizing neural network. To indicate that in this configuration of a trained deep learning framework, a separate machine learning algorithm module is provided for each modality type, an additional machine learning module 218 is shown, where that module may be a CNN, self-normalizing NN, or other type of trainable module. By way of example, the additional machine learning module 218 may be another image modality module, another molecular modality module, another clinical modality module, or any other suitable module such as an omics modality module receiving an omics modality dataset from a source. The embedding module 210 may be configured in different machine learning architectures to implement the functions of the neural networks 212, 214, 216, and 218. In some examples, the networks are implemented at separate neural networks each identifying respective features and embeddings and/or embedding predictions for each respective dataset. In some examples, the outputs of the separate neural networks may be combined in a fully connected layer. In other examples, each of these networks may be implemented as one or more specific internal layers in a neural network, where those layers may include embedding layers and one or more fully connected layers.

In some examples, each of the neural networks 212, 214, 216, and 218 are neural networks trained to first identify features within the respective received modality datasets and then perform a vectoring process to generate embeddings from these identified features. Example features are described herein including those in Tables 1 and 2. By way of example, image features may include identified tissue type, cell type, size, shape, and intensity, tumor shape, tumor minimum shape and max shape, tumor area, tumor perimeter, tumor percentage, cell shape, cell area, cell perimeter, cell convex area ratio, cell circularity, cell convex perimeter area, cell length, lymphocyte percentage, cellular characteristics, cell textures, including saturation, intensity, and hue. In some examples, these neural networks are trained to identify features as well as to generate the unimodal embeddings therefrom. In some examples, features are identified in the received modality datasets themselves and the neural networks are trained to generate the unimodal embeddings. In various examples, the neural networks 212, 214, 216, and 218 do not use all received features or generated features in determining the unimodal embedding predictions. In some examples, the embedding network 210 receives features from the modality datasets 204, 206, and 208 that are not used in determining the embeddings, and in some of these examples, such received features may be communicated to the loss minimization module 220 and/or embedding fusion module 226 and used to perform loss minimization, feature weighting, and embedded fusion to generate the multimodal embedding predictions not only from unimodal embeddings output from the neural networks 212, 214, 216, and 218, but additionally from other features not used in generating these embeddings.

The deep learning framework 200 further includes a loss minimization module 220 configured with two different loss processes. A multimodal orthogonalization loss process 222 is provided to establish orthogonalization across the embeddings from the embedding module 210 and connected layer loss process 224 to generate an outcome prediction.

The deep learning framework 200 further includes a multidimensional fusion module 226, which in the illustrated example is implemented as a gating-based attention fusion module that generates multimodal embedding predictions 228 and optionally a multidimensional tensor fusion 230.

Thus, in the illustrated example, the deep learning framework 200 is configured to combine radiology image data, pathology image data, molecular data, and optionally other data such as clinical data, to generate a fused prognostic risk score in the form of a multimodal embedding prediction. Modules 210, 220, and 226 combine to perform a deep orthogonal fusion that is trained to maximize the independent contribution of each modality dataset, effectively improving predictive performance over conventional combinational techniques. With the present techniques, efficient multimodal fusing of can be performed across image data, molecular data, and clinical data. Moreover, the multimodal fusion may be multidimensional, in that two or more different modality datasets may be combined. Moreover still, such multidimensionality allows for the deep learning framework to generate a set of embeddings that can be analyzed against each other to determine which are most accurate for prediction purpose. The set of embeddings may include unimodal, bi-modal, tri-modal, up to N-modal embeddings that may be compared against one another.

Figure 3:
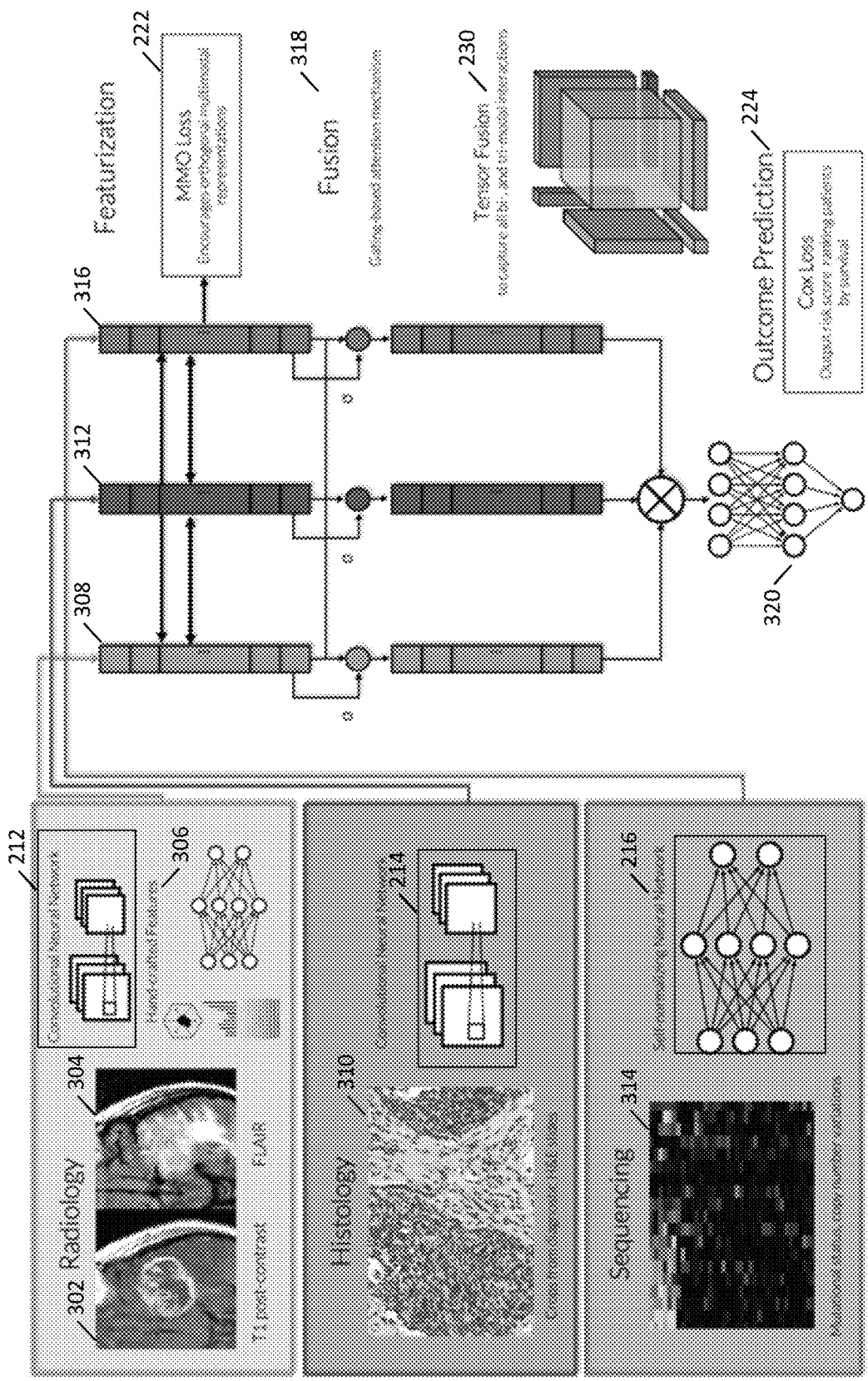
FIG. 3 illustrates an example implementation of the trained deep learning framework of FIG. 2, in accordance with an example.

FIG. 3 illustrates an implementation of the deep learning framework 200. In the illustrated the example, the radiomic image modality dataset 204 contains one or more MRI images 302 and FLAIR images 304, and the dataset may further include hand-crafted features 306 that have been identified in one or more of the images 302 and 304. These hand-crated features 306 may be manually labeled on the images or separately provided features, such as patterns of structures that may be contained within the radiomic image dataset. Collectively, the images 302/304 and the features 306 are provided to the radiomic image CNN 212 which generates a plurality of embeddings 308, only an example portion of which are shown for demonstration purposes. The pathology image modality dataset 206 contains one or more images 310 of H&E stained slides, where the images may be whole slide images or partial slide images. The image dataset 206 is provide to the pathology image CNN 214 which generates a plurality of embeddings 312, only an example portion of which are shown for demonstration purposes. The molecular modality dataset 208 contains gene sequencing read data 314 provided to the self-normalizing NN 216 which generates a plurality of embeddings 316, only an example portion of which are shown for demonstration purposes.

Figure 4:
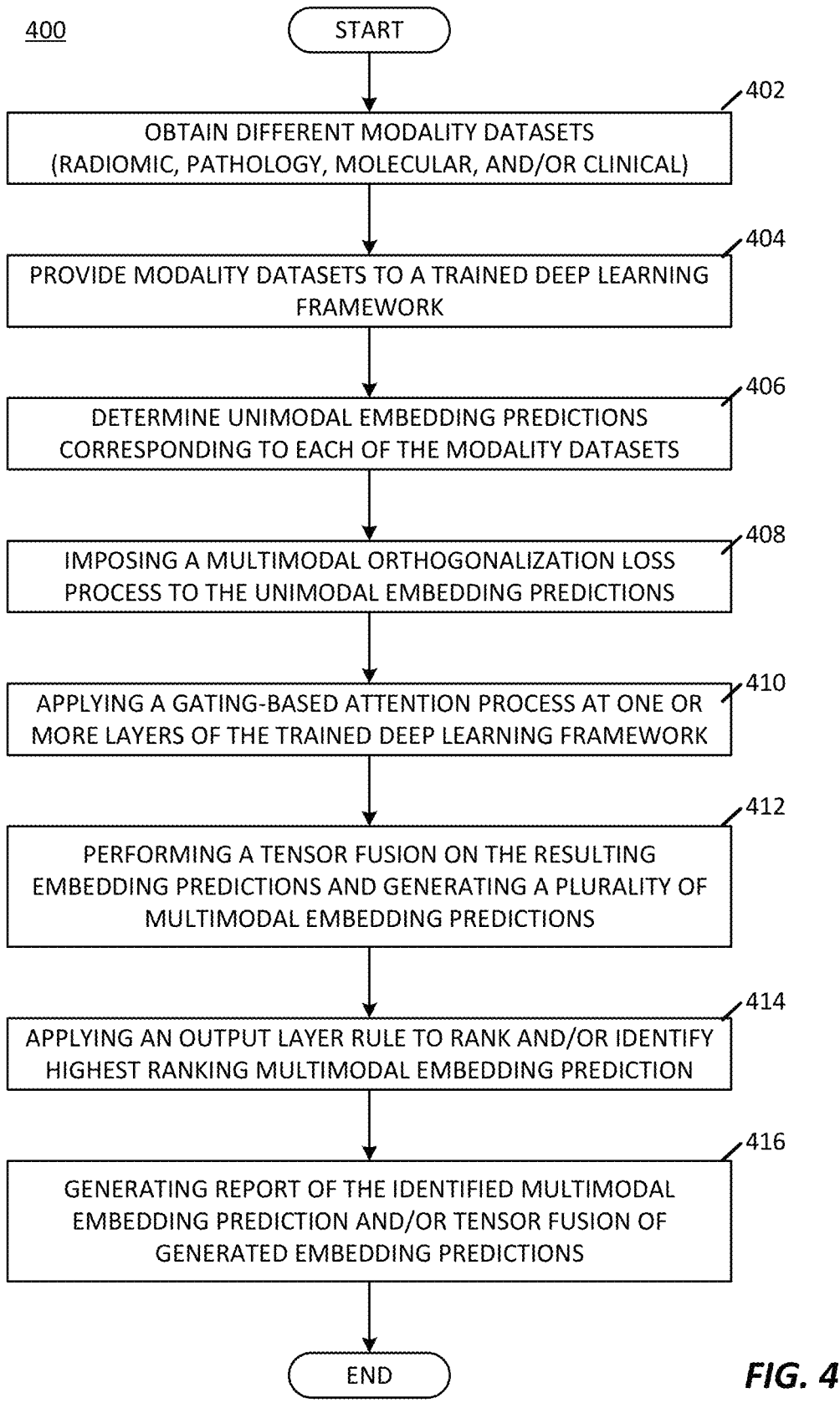
FIG. 4 illustrates is process for generating a multimodal embedding prediction using the trained deep learning framework of FIG. 2, in accordance with an example.

FIG. 4 illustrates a process 400 for determining a multimodal biomarker in accordance with the example of FIG. 3. Initially different modality datasets are received in a block 402 and the modality datasets are provided to the trained deep learning framework at a block 404. At a block 406, that deep learning framework determines unimodal embedding predictions, such as embeddings 308, 312, and 316, and, at a block 408, the deep learning framework imposes a multimodal orthogonalization loss process to these embeddings, reducing the number of embeddings to those with an orthogonal correlation to a predicted outcome. As shown in FIG. 3 this multimodal orthogonalization loss process can be applied between each of the different embedding predictions. Next, at a block 410, the deep learning framework applies a gating-based attention process across all the resulting embeddings from the loss process at block 408. This gating-based attention process imposes weighting factors on the resulting embeddings to allow for tensor fusion of the embeddings into various multimodal embeddings at a block 412. Each of the generated multimodal embeddings is a prediction of a state or outcome, such as patient survival. At a block 414, a rule is applied to rank the multimodal embeddings by risk score, e.g., by survival. For example, a maximum prediction score may be identified from the multimodal embeddings and that maximum score may be output as the multimodal embedding prediction. In other examples, an average prediction score may be output, or a prediction score corresponding to a given percentile value across all prediction scores (such as the prediction score at the 75$^{th}$ percentile of the generated prediction scores across all multimodal embedding predictions). In some of these various examples, the prediction scores for the unimodal embeddings are combined with the prediction scores of the multimodal embeddings to determine an output multimodal embedding prediction. In another example, the fusion model 226 may comprise an ensemble model for combining the scores from each model predictor of the multi-modal embeddings. Further aggregation may include, averaging, mean, min, max, or concatenation of the predictors. At a block 416, a report is generated of the identified multimodal embedding with the highest assurance score and/or of a tensor fusion of the various unimodal and multimodal embedding predictions generated by the foregoing processes.

Creating an orthogonalization amongst the embeddings 308, 312, and 316 may be performed to ensure that the multimodal embeddings 228 contain only those embeddings most correlative for prediction purposes. An implementation of the processes associated with the modules 210, 220, and 226 will now be described, demonstrating orthogonalization and fusion in reference to FIG. 3.

Initially, we describe example training for each of the different modality machine learning networks 212, 214, 216, and/or 218. Let X be a training mini-batch of data for N patients, each containing M modality datasets such that X=[$x_1$, $x_2$, . . . , $x_M$]. For each modality dataset m, $x_m$ includes data from for N patients. $\Phi_m$ denotes a trainable unimodal neural network (e.g., networks 212, 214, 216, and 218)), which accepts $x_m$ and generates a deep embedding $h_m \in \mathbb{R}^{l_1 \times N}$ as $h_m = \Phi_m(x_m)$. The multidimensional fusion module 226, when M>1, combines embeddings from each modality (e.g., embeddings from each neural network 212, 214, 216, and/or 218) in a multimodal fusion network. In an example, for each embedding, $h_m$, the fusion module 226 applies an attention process to control the expressiveness of that embedding based on information from the other modalities, that is, from the other unimodal embeddings. In an example, the attention process is a gating-based attention process such as one or more attention gated layers in a convolution neural network. An additional fully connected layer is applied to derive $h_m^S$ of length $l_2$. In some examples, the fusion module 226 obtains attention weightings of length $l_2$ through a bilinear transformation between $h_m$ with the other embeddings, then applied to $h_m^S$:

$$a_m = \sigma(h_m^T * W_A * [h_1, \ldots, h_{m-1}, h_{m+1}, \ldots, h_M])$$

$$h^*_m = a_m * h_m^S$$

To capture all possible interactions between different modality embeddings, in an example, the fusion module 226 combines attention-weighted embeddings through an outer product between modalities, known as tensor fusion process 318. In an example, a value of 1 is added to each vector, allowing for partial interactions between modality embeddings and for the constituent unimodal embeddings to be retained.

$$F = \begin{bmatrix} 1 \\ h_1^* \end{bmatrix} \otimes \begin{bmatrix} 1 \\ h_2^* \end{bmatrix} \otimes \cdots \otimes \begin{bmatrix} 1 \\ h_M^* \end{bmatrix}$$

The output matrix, F, is an M-dimensional hypercube 230 of all multimodal embedding interactions (i.e., combinations) with sides of length $l_2+1$. An example of F is depicted in FIG. 3 for the three different modality datasets, the radiology image dataset 204, the pathology image dataset 206, and molecular dataset 208, resulting in a 3D dimensional hypercube 230. In the event of larger numbers, N, of modalities, the resulting hypercube representing all multimodal embedding combinations would have N-dimensions. In any event, in an example implementation, the resulting fusion matrix 230 contains subregions corresponding to unaltered unimodal embeddings, pairwise fusions (e.g., multimodal embeddings between two of the modality datasets 204/206/208), and trilinear fusions (e.g., multimodal embeddings between all three modality datasets 204, 206, and 208). As illustrated, the fusion module 226 may be configured in some examples to generate a final set of fully connected layers 320, denoted by $\Phi_F$, which are applied to the tensor fusion features for a final fused embedding: $h_F = \Phi_F(F)$, which may represent one or more linear or nonlinear combinations, such as those described above with respect to fusion module 226.

To minimize converging of unimodal embeddings and to use embeddings that have dissociated effects on the predicted outcomes, the MMO process 222 is used to impose that the unimodal embeddings provided to the fusion module 226 are orthogonal. That is, in some examples, the orthogonality imposed by the process 222 represents varying degrees of orthogonalization, from completely orthogonal where there is no correlation between each unimodal embedding and varying amounts of partial (but not complete) correlation between unimodal embeddings. Notably for higher modal embeddings (bi-, tri- etc.), the orthogonalization may be imposed across any multimodal combination of embeddings, having the same modal number or a lower modal number. The orthogonalization criterion of the process 222, in some examples, enforces that each modality dataset introduced contributes unique information to outcome prediction, rather than relying on signal redundancy between modality datasets. In an example, each trained neural network (e.g., 212, 214, 216, and 218), $\Phi_m$, is updated through the MMO loss process 222 to yield embeddings that better complement other modalities. For example, let $H \in \mathbb{R}^{l_1 \times M * N}$ be the set of embeddings from all modalities. The process 222 may calculate an MMO loss as follows:

$$L_{MMO} = \frac{1}{M * N} \sum_{m=1}^{M} \max(1, \|h_m\|_*) - \|H\|_*$$

where $\|\cdot\|_*$ denotes the matrix nuclear norm (e.g., the sum of the matrix singular values). This loss is the difference between the sum of nuclear norms per embedding and the nuclear norm of all embeddings combined. The loss expression penalizes the scenario where the variance of two modality embeddings separately is decreased when combined and minimized when all unimodal embeddings are fully orthogonal. In an example, the per-modality norm is bounded to a minimum of 1 to prevent the collapse of embedding features to zero.

Each of the neural networks 212, 214, and 216, contains a final layer, parameterized by $\beta$, which is a fully connected layer with a single unit, which functions as a Cox proportional hazards model using the deep embedding from the previous layer, h, as its covariates. In this way, each final layer outputs a log hazard ratio $\theta$, which is used as a risk score and given for patient i by $\theta_i = h_i^T * \beta$, which is a prediction for the unimodal embedding, resulting in an embedding prediction output.

In an example of the loss process 224, a negative log likelihood is used as the cost function:

$$L_{pl} = -\sum_{i:E_i=1}\left(\theta_i - \log \sum_{j:t_j \geq t_i} e^{\theta_j}\right)$$

$t \in \mathbb{R}^{N \times 1}$ indicates the time to date of last follow up. The event vector, $E \in \{0, 1\}^{N \times 1}$, equals 1 if an event was observed (death) or 0 if a patient was censored (still alive) at time of last follow up. Each patient i with an observed event is compared against all patients whose observation time was greater than or equal to $t_i$. Training of the neural networks 212, 214, 216, and/or 218 is performed based on a combination of the two loss functions given by:

$$L = L_{pl} + \gamma L_{MMO}$$

where $\gamma$ is a scalar weighting the contribution of MMO loss relative to Cox partial likelihood loss. In examples, when training unimodal networks, the value of $\gamma$ is set to zero.

EXAMPLE

Figure 5:
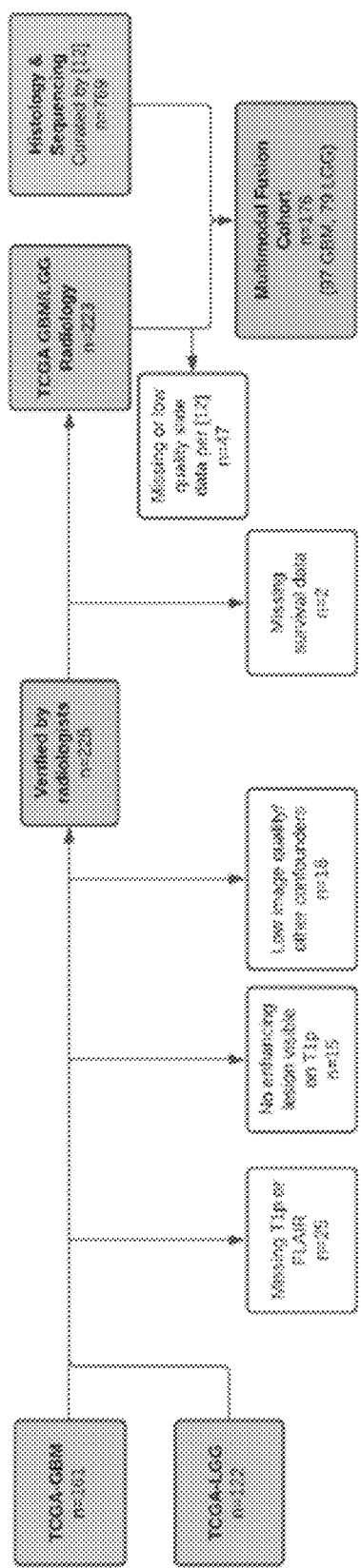
FIG. 5 illustrates radiomic image datasets for an example implementation of the present techniques on a sample size of 176 patients, in accordance with an example.

Radiomic datasets: in a working example, a radiology image dataset containing radiology images for 176 patients (see, FIG. 5) with Gd-T1w and T2w-FLAIR scans from the TCGA-GBM study were obtained and annotated by 7 radiologists to delineate the enhancing lesion and edema region. MRI scans were registered to the MNI-ICBM standardized brain atlas with 1 mm isotropic resolution, processed with N4 bias correction, and intensity normalized. CNN inputs in the form of 96×96×3 patches were generated from matching regions of Gd-T1w and T2w-FLAIR images within the enhancing lesion. For each patient, 4 samples were generated from the four quadrants of the tumor along the Z axis. Patch position was randomized in unimodal training (e.g., of the deep learning framework in particular of the training of networks 212 and/or 214) and fixed to the middle of the quadrants during inference and fusion network training (e.g., training of fusion module 226). Feature input: Nine explicit features (including size, shape, and intensity measures were extracted separately from Gd-T1w and T2w-FLAIR images, and summarized in 3 different fashions for a total of 56 handcrafted features e.g., features 306), listed in Table 1.

TABLE 1

List of handcrafted radiology features

| Feature name/number | Feature Description | Summarization of annotated regions |
|---|---|---|
| No. regions (f1, f2) | # annotated lesions on T1, edema on FLAIR | N/A |
| Volume (f3-f8) | Volume of 3D, ROI, measured in mm^3 | sum, max, & avg on T1p and FLAIR |
| Longest axis (f9-f14) | Longest distance between a contour's vertices | sum, max, & avg on T1p and FLAIR |
| SA/V Ratio (f15-f20) | Ratio of the surface area to volume. | sum, max, & avg on T1p and FLAIR |
| Sphericity (f21-f26) | How closely a region's shape resembles a sphere | sum, max, & avg on T1p and FLAIR |
| Mean I (f27-f32) | Mean intensity in contoured region | sum, max, & avg on T1p and FLAIR |
| $10^{th}$ percentile (f33-f38) | $10^{th}$ % of intensities in contoured region | sum, max, & avg on T1p and FLAIR |
| $90^{th}$ percentile (f39-f44) | $90^{th}$ % of intensities in contoured region | sum, max, & avg on T1p and FLAIR |
| Skewness (f45-f50) | Skewness of intensities in contoured region | sum, max, & avg on T1p and FLAIR |
| Variance (f51-f56) | Variance of intensities in contoured region | sum, max, & avg on T1p and FLAIR |

Pathology datasets and Molecular (e.g., genomics) datasets: in an example, we obtained 1024×1024 normalized regions-of-interest (ROIs) from diagnostic H&E slide images. Each patient had 1-3 ROIs from diagnostic slide images, for a total of 372 pathology images. In one example, a plurality of copy number variations and mutational status may be curated from the same set, as the molecular dataset.

Clinical datasets: 14 clinical features were included into a self-normalizing neural network (SNN) (e.g., an implementation of the additional machine learning module 218) for the prediction of prognosis. The feature set included demographic, treatment, and subjective histological subtype, and is listed in Table 2.

TABLE 2

List of clinical features

| Variable | Value Type |
|---|---|
| Age (f1) | Continuous |
| Karnofsky Performance Score (f2) | Continuous |
| Grade (f3) | Categorical |
| Sex: Male vs. Female (f4) | Binary |
| Treatment: any (f5), radiation (f6), chemotherapy (f7) | Binary |
| Histological diagnosis: LGG (f8), Astrocytoma (f9), Glioblastoma (f10), Oligoastrocytoma (f11), Oligodendroglioma (f12) | Binary |
| Race/ethnicity: White vs. Non-white (f13), Hispanic vs. Non-Hispanic (f14) | Binary |

Implementation Details: The embedding size for the unimodal networks (e.g., 212, 214, 216, and 218), $l_1$, was set to 32. Pre-fusion scaled embedding size, $l_2$, such as the length of the vector resulting from the embedding models includes 32, 16, and 8 to optimize the computational complexity based on the training time desired, whereas a higher length takes longer to train but provides greater dimensionality of the intermediate layers in the model. Post-fusion fully connected layers consisted of 128 units each unimodal network. The final layer of each network had a single unit with sigmoid activation, but its outputs were rescaled between −3 and 3 to function as a prognostic risk score. Unimodal networks (e.g., of the embedding module 210) were trained for 50 epochs with linear learning rate decay, while multimodal networks (e.g., of the fusion module 226) were trained for 30 epochs with learning rate decay beginning at the 10th epoch. When training multimodal networks, the unimodal embedding layers were frozen for 5 epochs to train the fusion layers only, then unfrozen for joint training of embeddings and fusion layers.

Figure 6:
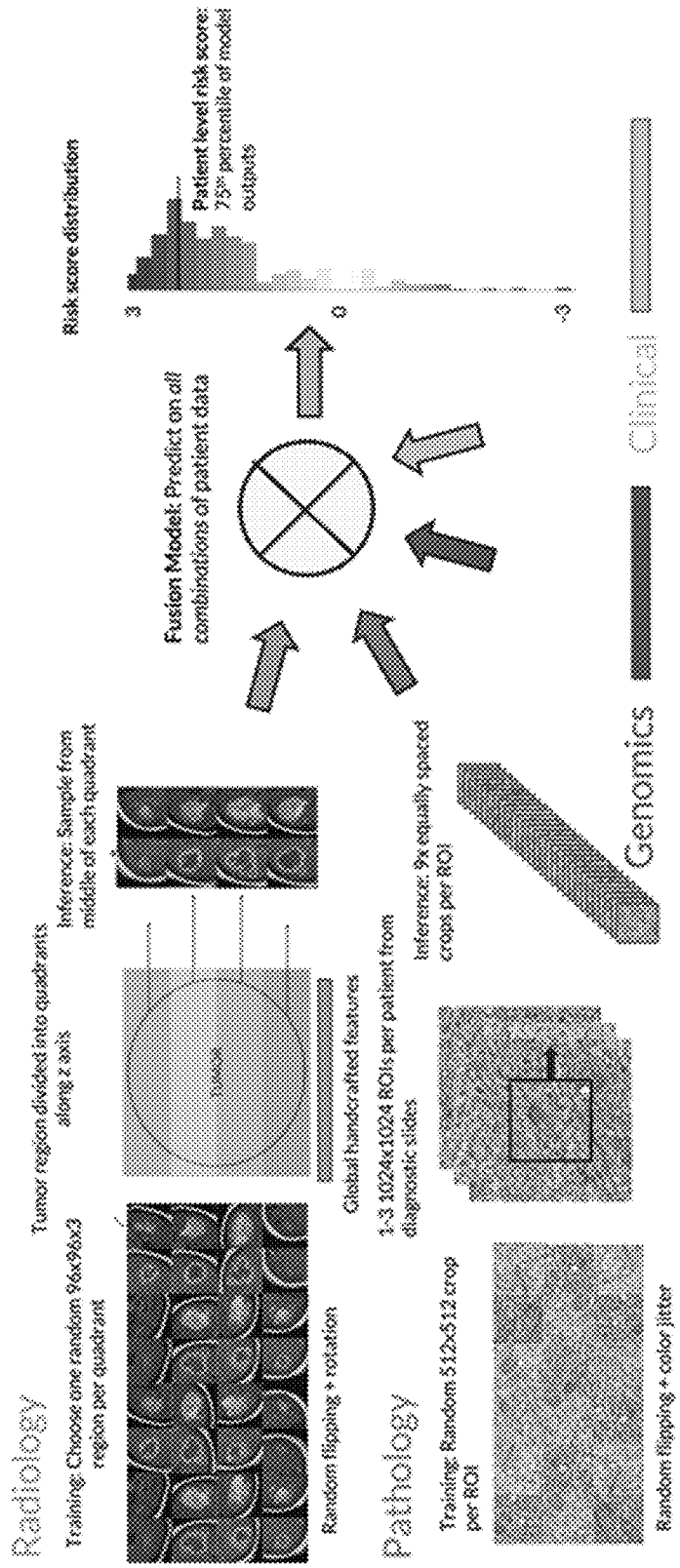
FIG. 6 illustrates a sampling strategy that may be used to identify regions of interest and features within radiomic modality image data, pathology modality image data, genomic modality data, and clinical modality data, in accordance with an example.

Statistical Analysis: All models were trained via 15-fold Monte Carlo cross-validation with 20% holdout using the patient level splits. The primary performance metric was the median observed concordance index (c-index) across folds, a global metric of prognostic model discriminant power. We evaluated all possible combinations of a patient's data (see sampling strategy in FIG. 6) and used the 75th percentile of predicted risk score as their overall prediction. Binary low/high risk groups are derived from the risk scores, where a risk score>0 corresponded to high risk. For Kaplan Meier (KM) curves, patient-level risk scores were pooled across validation folds for KM curves and multivariable testing for independence with clinical variables in a Cox proportional hazards model.

Example—Results

In this example, we compared unimodal embeddings against different multimodal embeddings, as shown in Table 3 ("Rad"— radiology-data based embedding, "Path"— pathology-date based embedding, "Gen"—molecular-data based embedding, and "Clin"—clinical-data based embedding). The unimodal molecular embedding, determined from the molecular dataset, and the unimodal pathology embedding, determined from the pathology image dataset, resulted in prediction results that were about the same. For the radiology dataset, CNN-only (C-index=0.687+/−0.067) and feature-only (C-index=0.653+/−0.057) radiology unimodal embeddings underperformed relative to the unimodal molecular embedding and unimodal pathology embedding. However, combining the radiology CNN features with the handcrafted features resulted in the strongest unimodal embedding predictions. Clinical dataset (e.g., with clinical features) resulted in the least prognostic unimodal embedding.

TABLE 3

| Group | Model | Cox Loss Only | With MMO Loss |
|---|---|---|---|
| Unimodal | Rad | 0.718 ± 0.064 | — |
| | Path | 0.715 ± 0.054 | — |
| | Gen | 0.716 ± 0.063 | — |
| | Clin | 0.702 ± 0.049 | — |
| Pairwise Fusion | Path + Gen | 0.711 ± 0.055 | 0.752 ± 0.072 |
| | Gen + Clin | 0.702 ± 0.053 | 0.703 ± 0.052 |
| | Rad + Gen | 0.761 ± 0.071 | 0.766 ± 0.067 |
| | Rad + Path | 0.742 ± 0.067 | 0.752 ± 0.072 |
| | Rad + Clin | 0.746 ± 0.068 | 0.736 ± 0.067 |
| | Path + Clin | 0.696 ± 0.051 | 0.690 ± 0.043 |
| Triple Fusion | Path + Gen + Clin | 0.704 ± 0.059 | 0.720 ± 0.056 |
| | Rad + Path + Clin | 0.748 ± 0.067 | 0.741 ± 0.067 |
| | Rad + Gen + Clin | 0.754 ± 0.066 | 0.755 ± 0.067 |
| | Rad + Path + Gen | 0.764 ± 0.062 | 0.788 ± 0.067 |
| Full Fusion | Rad + Path + Gen + Clin | 0.775 ± 0.061 | 0.785 ± 0.077 |

As shown, using the trained deep learning framework herein, with deep fusion models integrating radiology modality datasets with other modality datasets, outperformed unimodal embeddings, naive combinations of unimodal models, as well as fusions utilizing only clinical and/or biopsy-derived modalities. The full fusion embedding in Table 3, that is, the multimodal embedding combining all four modality datasets (c-index=0.775±0.061) achieved the best performance when trained with Cox loss only. Naive ensembles averaging predictions from the same modalities were inferior in performance (c-index=0.739±0.062 and 0.735±0.063, respectively), confirming the benefits of a deep fusion approach.

The addition of the MMO loss to the training of the deep fusion models consistently improved the predictive performance at five different weightings (Table 4) (("Rad"— radiology-data based embedding, "Path"—pathology-date based embedding, and "Seq"—molecular-data based embedding, and "Clin"—clinical-data based embedding), with best performance for both at γ=0.5. When all fusion models are trained at this weighting, 8 of 11 improve in performance (see, Table 3). Deep orthogonal fusion, e.g., applying MMO loss), resulted in a multimodal embedding combining radiology, pathology, and genomic data predicted glioma survival best overall with a median c-index of 0.788+/−0.067.

TABLE 4

Performance of top fusion models with various weightings of orthogonality loss

| γ | Rad + Path + Seq | Rad + Path + Seq + Clin |
|---|---|---|
| 0 | 0.764 +/− 0.062 | 0.775 +/− 0.061 |
| .1 | 0.768 +/− 0.064 | 0.745 +/− 0.068 |
| .25 | 0.777 +/− 0.066 | 0.782 +/− 0.066 |
| .5 | 0.788 +/− 0.067 | 0.785 +/− 0.077 |
| 1 | 0.779 +/− 0.070 | 0.776 +/− 0.075 |
| 2.5 | 0.781 +/− 0.073 | 0.760 +/− 0.072 |

Figure 7C:
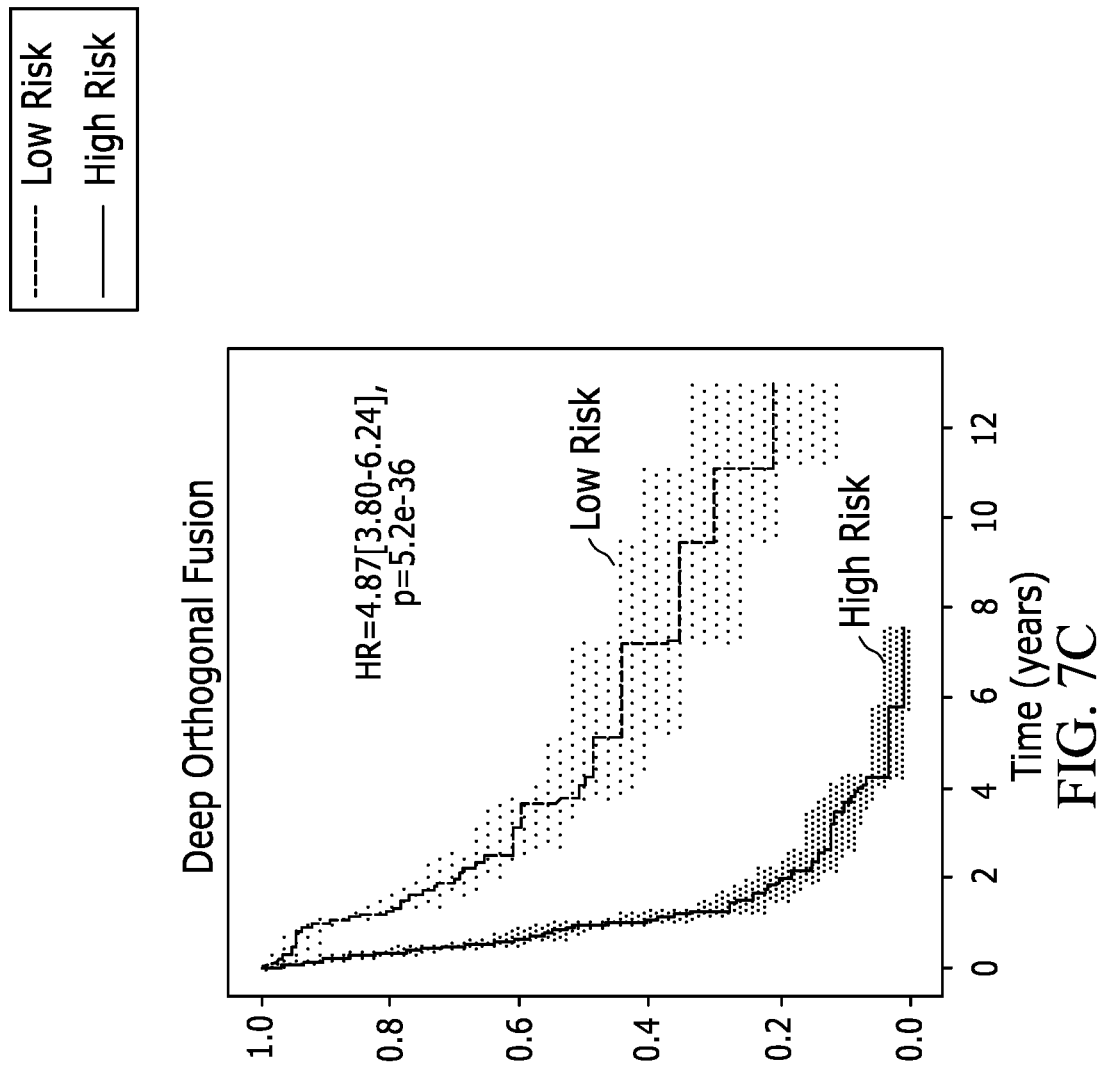
FIG. 7C shows the orthogonal fusion risk groups derived from a multimodal embedding prediction based on radiology, pathology, and molecular data, according to this example of the present techniques.
Figures 8A, 8B:
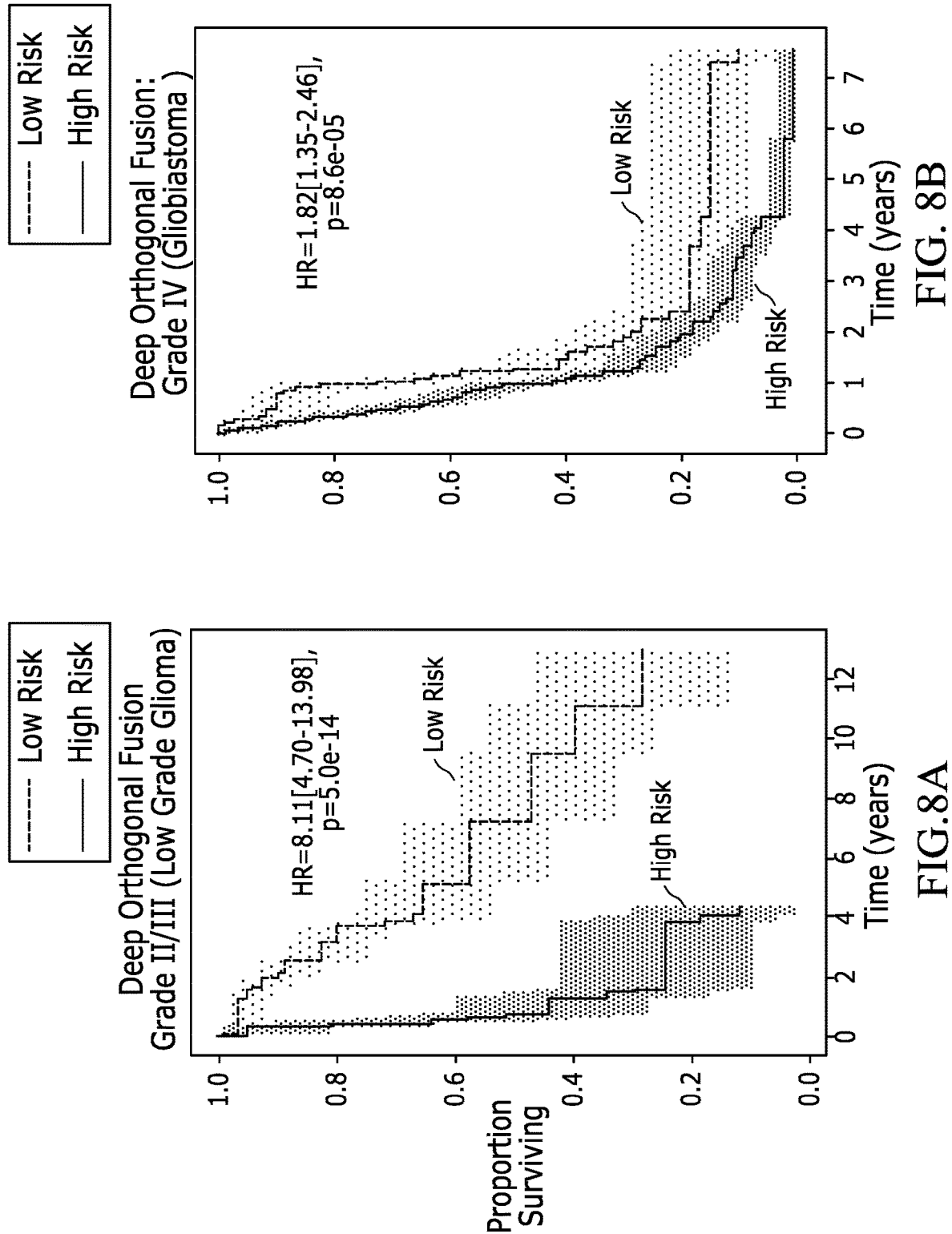

In FIGS. 7A-7C, Kaplan Meier plots show that the stratification of patients by OS in risk groups derived from this model performs comparably to established prognostic clinical markers. FIG. 7A shows the stratification of glioma patients by grade. FIG. 7B shows the IDH (Isocitrate dehydrogenase) mutation status. FIG. 7C shows the orthogonal fusion risk groups derived from a multimodal embedding prediction based on radiology, pathology, and molecular data, according to this example of the present techniques. In FIGS. 8A-8D, Kaplan Meier plots show that with the deep orthogonal fusion techniques herein risk groups further stratify prognostic clinical subsets (grade, IDH status) by overall survival (OS). FIGS. 8A-8D illustrate the deep orthogonal fusion risk groups stratify patients by overall survival into subsets according to their grade, Grade II/III (FIG. 8A) and Grade IV (FIG. 8B) and according to IDH status, IDH mutation (FIG. 8C) and IDH wild type (FIG. 8D).

It is noted that while example deep learning frameworks 150/200 and neural networks 212/214/216/218 herein have been described as configured with example machine learning architectures (CNN configurations and self-normalization NN configurations), any number of suitable convolutional neural network architectures may be used. Broadly speaking, the deep learning frameworks herein may implement any suitable statistical model (e.g., a neural network or other model implemented through a machine learning process) that will be applied to each of the received image data, molecular data, and clinical data. As discussed herein, that statistical model may be implemented in a variety of manners. In some examples, machine learning is used to evaluate training images and develop classifiers that correlate predetermined image features to specific predictive outcomes, such as overall survival rate. In some examples, image features can be identified as training classifiers using a learning algorithm such as Neural Network, Support Vector Machine (SVM) or other machine learning process. Once classifiers within the statistical model are adequately trained with a series of training images, a series of molecular datasets, or a series of clinical datasets, the statistical model may be employed in real time to analyze subsequent images, subsequent molecular datasets, or subsequent clinical datasets provided as input to the statistical model for determining a multidimensional biomarker and for predicting state or outcomes. In some examples, when a statistical model is implemented using a neural network, the neural network may be configured in a variety of ways. In some examples, the neural network may be a deep neural network and/or a convolutional neural network. In some examples, the neural network can be a distributed and scalable neural network. The neural network may be customized in a variety of manners, including providing a specific top layer such as but not limited to a logistics regression top layer. A convolutional neural network can be considered as a neural network that contains sets of nodes with tied parameters. A deep convolutional neural network can be considered as having a stacked structure with a plurality of layers. The neural network or other machine learning processes may include many different sizes, numbers of layers and levels of connectedness. Some layers can correspond to stacked convolutional layers (optionally followed by contrast normalization and max-pooling) followed by one or more fully-connected layers. For neural networks trained by large datasets, the number of layers and layer size can be increased by using dropout to address the potential problem of overfitting. In some instances, a neural network can be designed to forego the use of fully connected upper layers at the top of the network. By forcing the network to go through dimensionality reduction in middle layers, a neural network model can be designed that is quite deep, while dramatically reducing the number of learned parameters. Further in examples herein, the neural network model may include at least attention gated layer, that applies attention weights to different features to increase their focus between layers.

Figure 9:
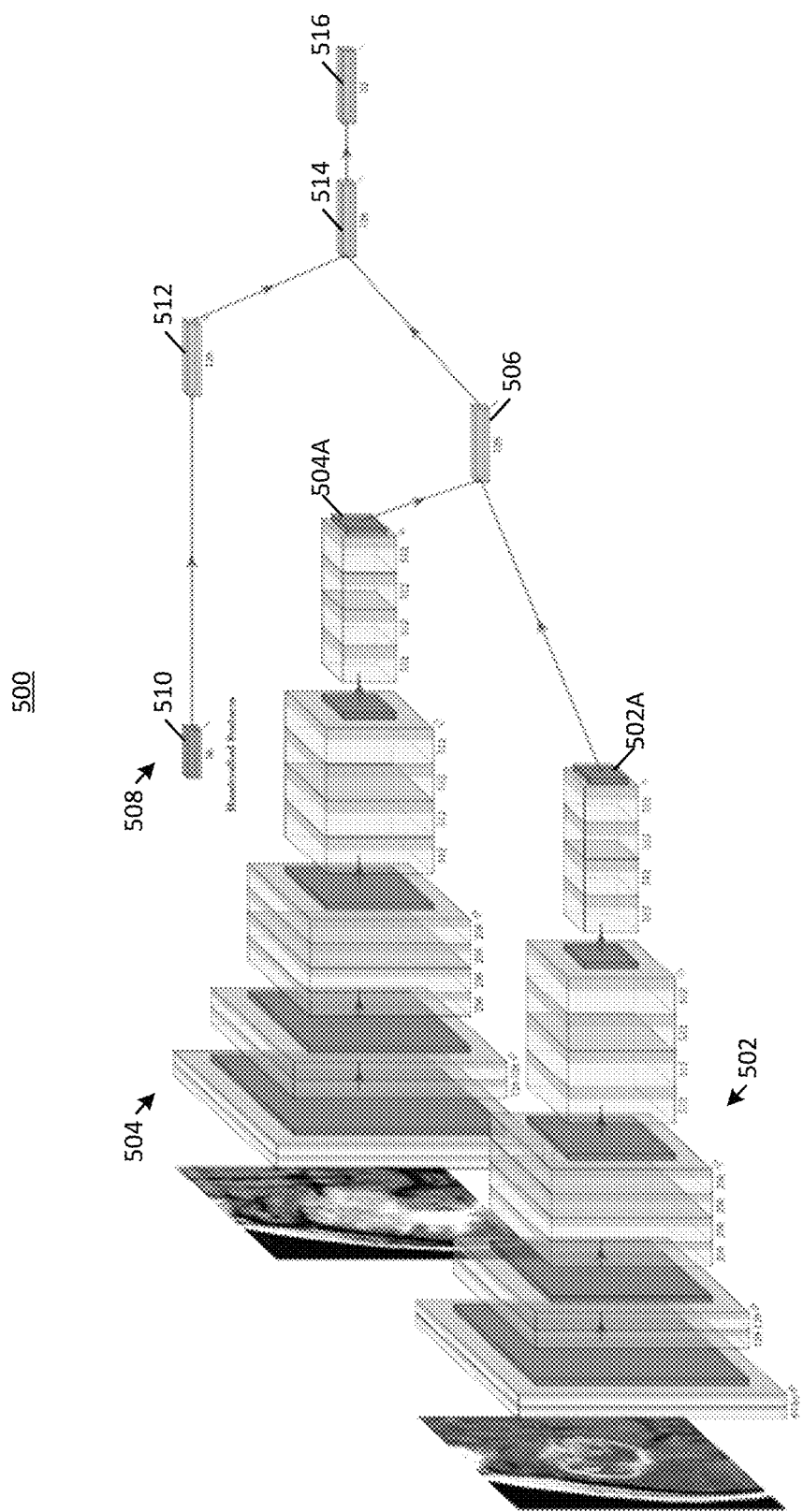
FIG. 9 is a schematic of an architecture for an example image modality neural network as may be implemented in the systems of FIGS. 1 and 2, in accordance with an example.

FIG. 9 illustrates an example implementation of a radiomic image modality convolution neural network, as may be implemented as the network 212. A neural network architecture 500 capable of condensing CNN-extracted deep features from local tumor regions on multiple radiomic image sequences (e.g., on Gd-T1w and FLAIR scans) with global hand-crafted features extracted across a full 3D region-of-interest. The neural network architecture 500 is configured as a multiple-input CNN designed to incorporate multiparametric radiomic image data (such as MRI data) and features, such as global lesion measurements. In an example, the backbone of the neural network architecture 500 is formed of two VGG-19 CNNs 502 and 504, with batch normalization, substituting the final max pooling layer with a 4×4 adaptive average pooling (502A and 504A, respectively). In some examples, the CNN configuration of the architecture 500 has been trained using multiparametric MRI training images and with labeled image features. While of the branches 502 and 504 are shown with a VGG-19 CNN configuration, other CNN configurations may be used. As shown, the two pre-trained CNN branches 502 and 504 separately extract features from different images, namely MRI, T1 contrast images such as Gd-T1w and FLAIR images such as T2w-FLAIR images, respectively. The outputs of these two branches 502 and 504 are then concatenated and passed through a fully connected layer 506. In the architecture 500, a third branch 508 passes hand-crafted features 510 (e.g., 56 features) through a similar fully connected layer 512. Concatenated embeddings from all branches 502, 502, and 508 are fed to two additional dense layers 514 and 516. Each fully connected layer 506, 512, and 514 preceding the final embedding layer 516, has 128 units. The final embedding layer 516 contains the unimodal radiomic embeddings, that are to be fed to loss minimization and embedded fusions processes for combining with unimodal embeddings from other neural networks.

As described, in various examples, the present techniques include systems and methods for deep orthogonal fusion, providing a data efficient mechanism for the fusion of different modality datasets, in particular, radiology, histology, genomic, and clinical data to derive novel multimodal prognostic biomarkers. In an example, we show that the integration of multi-dimensional data from biopsy-based modalities and radiology strongly boosts the ability to stratify glioma patients by overall survival. The introduction of a MMO loss component, which forces unimodal embeddings to provide independent and complementary information to the fused prediction, further improved prognostic performance of the deep orthogonal fusion. For example, the orthogonal fusion model incorporating radiology, histology, and genomic data significantly stratified glioma patients by overall survival within outcome-associated subsets, and added an important layer of granularity to what clinical grade and molecular subtypes currently offer. Advantageously, the deep orthogonal fusion can be applied to any number of cancer domains, modality combinations, or new clinical endpoints including treatment response prediction. Example cancer domains include but are not limited to, adrenocortical carcinoma, lymphoma, anal cancer, anorectal cancer, basal cell carcinoma, skin cancer (non-melanoma), biliary cancer, extrahepatic bile duct cancer, intrahepatic bile duct cancer, bladder cancer, urinary bladder cancer, osteosarcoma, brain tumor, brain stem glioma, breast cancer (including triple negative breast cancer), cervical cancer, colon cancer, colorectal cancer, lymphoma, endometrial cancer, esophageal cancer, gastric (stomach) cancer, head and neck cancer, hepatocellular (liver) cancer, kidney cancer, renal cancer, lung cancer, melanoma, cancer of the tongue, oral cancer, ovarian cancer, pancreatic cancer, prostate cancer, uterine cancer, testicular cancer, and vaginal cancer.

FIG. 10 illustrates an example computing device 600 for implementing the prediction system 100 and in particular the multimodal biomarker prediction system 102 of FIG. 1. As illustrated, the system 102 may be implemented on the computing device 600 and in particular on one or more processing units 610, which may represent Central Processing Units (CPUs), and/or on one or more or Graphical Processing Units (GPUs) 611, including clusters of CPUs and/or GPUs, and/or one or more tensor processing unites (TPU) (also labeled 611), any of which may be cloud based. Features and functions described for the system 102 may be stored on and implemented from one or more non-transitory computer-readable media 612 of the computing device 600. The computer-readable media 612 may include, for example, an operating system 614 and the deep learning framework 616 having elements corresponding to that of the deep learning framework 150 and/or the deep learning framework 200, including the pre-processing controllers, classifiers, embedding modules, loss minimization modules, and embedding fusion modules therein. More generally, the computer-readable media 612 may store trained deep learning models, executable code, etc. used for implementing the techniques herein. The computer-readable media 612 and the processing units 610 and TPU(S)/GPU(S) 611 may store pathology images and data and radiology images and data (including tissue classification data, cell segmentation data, etc. for these different modalities), and other modality data such as molecular data and clinical data in one or more databases 613. The computing device 600 includes a network interface 624 communicatively coupled to the network 650, for communicating to and/or from a portable personal computer, smart phone, electronic document, tablet, and/or desktop personal computer, or other computing devices. The computing device further includes an I/O interface 626 connected to devices, such as digital displays 628, user input devices 630, etc. In some examples, as described herein, the computing device 600 generates biomarker prediction as an electronic document 615 that can be accessed and/or shared on the network 650. In the illustrated example, the multimodal biomarker prediction system 102 is implemented on a single server 600. However, the functions of the system 102 may be implemented across distributed devices 600, 602, 604, etc. connected to one another through a communication link. In other examples, functionality of the system 102 may be distributed across any number of devices, including the portable personal computer, smart phone, electronic document, tablet, and desktop personal computer devices shown. In other examples, the functions of the system 102 may be cloud based, such as, for example one or more connected cloud TPU(s) customized to perform machine learning processes. The network 650 may be a public network such as the Internet, private network such as research institution's or corporation's private network, or any combination thereof. Networks can include, local area network (LAN), wide area network (WAN), cellular, satellite, or other network infrastructure, whether wireless or wired. The network can utilize communications protocols, including packet-based and/or datagram-based protocols such as internet protocol (IP), transmission control protocol (TCP), user datagram protocol (UDP), or other types of protocols. Moreover, the network can include a number of devices that facilitate network communications and/or form a hardware basis for the networks, such as switches, routers, gateways, access points (such as a wireless access point as shown), firewalls, base stations, repeaters, backbone devices, etc.

The computer-readable media may include executable computer-readable code stored thereon for programming a computer (e.g., comprising a processor(s) and GPU(s)) to the techniques herein. Examples of such computer-readable storage media include a hard disk, a CD-ROM, digital versatile disks (DVDs), an optical storage device, a magnetic storage device, a ROM (Read Only Memory), a PROM (Programmable Read Only Memory), an EPROM (Erasable Programmable Read Only Memory), an EEPROM (Electrically Erasable Programmable Read Only Memory) and a Flash memory. More generally, the processing units of the computing device 600 may represent a CPU-type processing unit, a GPU-type processing unit, a TPU-type processing unit, a field-programmable gate array (FPGA), another class of digital signal processor (DSP), or other hardware logic components that can be driven by a CPU.

Thus, as provided, a system for performing the methods described herein may include a computing device, and more particularly may be implemented on one or more processing units, for example, Central Processing Units (CPUs), and/or on one or more or Graphical Processing Units (GPUs), including clusters of CPUs and/or GPUs. Features and functions described may be stored on and implemented from one or more non-transitory computer-readable media of the computing device. The computer-readable media may include, for example, an operating system and software modules, or "engines," that implement the methods described herein. More generally, the computer-readable media may store batch normalization process instructions for the engines for implementing the techniques herein. The computing device may be a distributed computing system, such as an Amazon Web Services cloud computing solution.

The functions of the engines may be implemented across distributed computing devices, etc. connected to one another through a communication link. In other examples, functionality of the system may be distributed across any number of devices, including the portable personal computer, smart phone, electronic document, tablet, and desktop personal computer devices shown. The computing device may be communicatively coupled to the network and another network. The networks may be public networks such as the Internet, a private network such as that of a research institution or a corporation, or any combination thereof. Networks can include, local area network (LAN), wide area network (WAN), cellular, satellite, or other network infrastructure, whether wireless or wired. The networks can utilize communications protocols, including packet-based and/or datagram-based protocols such as Internet protocol (IP), transmission control protocol (TCP), user datagram protocol (UDP), or other types of protocols. Moreover, the networks can include a number of devices that facilitate network communications and/or form a hardware basis for the networks, such as switches, routers, gateways, access points (such as a wireless access point as shown), firewalls, base stations, repeaters, backbone devices, etc.

The methods and systems described above may be utilized in combination with or as part of a digital and laboratory health care platform that is generally targeted to medical care and research. It should be understood that many uses of the methods and systems described above, in combination with such a platform, are possible. One example of such a platform is described in U.S. Patent Publication No. 2021/0090694, titled "Data Based Cancer Research and Treatment Systems and Methods", and published Mar. 25, 2021, which is incorporated herein by reference and in its entirety for any and all purposes.

For example, an implementation of one or more embodiments of the methods and systems as described above may include microservices constituting a digital and laboratory health care platform supporting immunotherapy response prediction from H&E images or other pathology images sources. Embodiments may include a single microservice for executing and delivering immunotherapy response prediction or may include a plurality of microservices each having a particular role which together implement one or more of the embodiments above. In one example, a first microservice may execute H&E image analysis and molecule location prediction in order to deliver predicted molecule locations to a second microservice for analyzing number and location of predicted molecules. Similarly, the second microservice may execute analysis of predicted molecule locations to deliver immunotherapy response prediction according to an embodiment, above.

Where embodiments above are executed in one or more micro-services with or as part of a digital and laboratory health care platform, one or more of such micro-services may be part of an order management system that orchestrates the sequence of events as needed at the appropriate time and in the appropriate order necessary to instantiate embodiments above. A micro-services based order management system is disclosed, for example, in U.S. Patent Publication No. 2020/80365232, titled "Adaptive Order Fulfillment and Tracking Methods and Systems", and published Nov. 19, 2020, which is incorporated herein by reference and in its entirety for all purposes.

For example, continuing with the above first and second microservices, an order management system may notify the first microservice that an order for H&E image analysis and molecule location prediction has been received and is ready for processing. The first microservice may execute and notify the order management system once the delivery of predicted molecule locations is ready for the second microservice. Furthermore, the order management system may identify that execution parameters (prerequisites) for the second microservice are satisfied, including that the first microservice has completed, and notify the second microservice that it may continue processing the order to analyze predicted molecule locations and generate immunotherapy response prediction according to an embodiment, above.

Where the digital and laboratory health care platform further includes a genetic analyzer system, the genetic analyzer system may include targeted panels and/or sequencing probes. An example of a targeted panel is disclosed, for example, in U.S. Patent Publication No. 2021/0090694, titled "Data Based Cancer Research and Treatment Systems and Methods", and published Mar. 25, 2021, which is incorporated herein by reference and in its entirety for all purposes. An example of a targeted panel for sequencing cell-free (cf) DNA and determining various characteristics of a specimen based on the sequencing is disclosed, for example, in U.S. patent application Ser. No. 17/179,086, titled "Methods And Systems For Dynamic Variant Thresholding In A Liquid Biopsy Assay", and filed Feb. 18, 2021, U.S. patent application Ser. No. 17/179,267, titled "Estimation Of Circulating Tumor Fraction Using Off-Target Reads Of Targeted-Panel Sequencing", and filed Feb. 18, 2021, and U.S. patent application Ser. No. 17/179,279, titled "Methods And Systems For Refining Copy Number Variation In A Liquid Biopsy Assay", and filed Feb. 18, 2021 which is incorporated herein by reference and in its entirety for all purposes. In one example, targeted panels may enable the delivery of next generation sequencing results (including sequencing of DNA and/or RNA from solid or cell-free specimens) according to an embodiment, above. An example of the design of next-generation sequencing probes is disclosed, for example, in U.S. Patent Publication No. 2021/0115511, titled "Systems and Methods for Next Generation Sequencing Uniform Probe Design", and published Jun. 22, 2021 and U.S. patent application Ser. No. 17/323,986, titled "Systems and Methods for Next Generation Sequencing Uniform Probe Design", and filed May 18, 2021, which are incorporated herein by reference and in their entirety for all purposes.

Where the digital and laboratory health care platform further includes an epigenetic analyzer system, the epigenetic analyzer system may analyze specimens to determine their epigenetic characteristics and may further use that information for monitoring a patient over time. An example of an epigenetic analyzer system is disclosed, for example, in U.S. patent application Ser. No. 17/352,231, titled "Molecular Response And Progression Detection From Circulating Cell Free DNA", and filed Jun. 18, 2021, which is incorporated herein by reference and in its entirety for all purposes.

Where the digital and laboratory health care platform further includes a bioinformatics pipeline, the methods and systems described above may be utilized after completion or substantial completion of the systems and methods utilized in the bioinformatics pipeline. As one example, the bioinformatics pipeline may receive next-generation genetic sequencing results and return a set of binary files, such as one or more BAM files, reflecting DNA and/or RNA read counts aligned to a reference genome.

When the digital and laboratory health care platform further includes an RNA data normalizer (or any other molecular data normalier), any RNA read counts may be normalized before processing embodiments as described above. An example of an RNA data normalizer is disclosed, for example, in U.S. Patent Publication No. 2020/0098448, titled "Methods of Normalizing and Correcting RNA Expression Data", and published Mar. 26, 2020, which is incorporated herein by reference and in its entirety for all purposes.

When the digital and laboratory health care platform further includes a genetic data deconvolver, any system and method for deconvolving may be utilized for analyzing genetic data associated with a specimen having two or more biological components to determine the contribution of each component to the genetic data and/or determine what genetic data would be associated with any component of the specimen if it were purified. An example of a genetic data deconvolver is disclosed, for example, in U.S. Patent Publication No. 2020/0210852, published Jul. 2, 2020, and PCT/US19/69161, filed Dec. 31, 2019, both titled "Transcriptome Deconvolution of Metastatic Tissue Samples"; and U.S. patent application Ser. No. 17/074,984, titled "Calculating Cell-type RNA Profiles for Diagnosis and Treatment", and filed Oct. 20, 2020, the contents of each of which are incorporated herein by reference and in their entirety for all purposes.

RNA expression levels (or other molecular data levels) may be adjusted to be expressed as a value relative to a reference expression level. Furthermore, multiple RNA expression data sets may be adjusted, prepared, and/or combined for analysis and may be adjusted to avoid artifacts caused when the data sets have differences because they have not been generated by using the same methods, equipment, and/or reagents. An example of RNA data set adjustment, preparation, and/or combination is disclosed, for example, in U.S. patent application Ser. No. 17/405,025, titled "Systems and Methods for Homogenization of Disparate Datasets", and filed Aug. 18, 2021.

When the digital and laboratory health care platform further includes an automated RNA expression caller, RNA expression levels associated with multiple samples may be compared to determine whether an artifact is causing anomalies in the data. An example of an automated RNA expression caller is disclosed, for example, in U.S. Pat. No. 11,043,283, titled "Systems and Methods for Automating RNA Expression Calls in a Cancer Prediction Pipeline", and issued Jun. 22, 2021, which is incorporated herein by reference and in its entirety for all purposes.

The digital and laboratory health care platform may further include one or more insight engines to deliver information, characteristics, or determinations related to a disease state that may be based on genetic and/or clinical data associated with a patient, specimen and/or organoid. Exemplary insight engines may include a tumor of unknown origin (tumor origin) engine, a human leukocyte antigen (HLA) loss of homozygosity (LOH) engine, a tumor mutational burden engine, a PD-L1 status engine, a homologous recombination deficiency engine, a cellular pathway activation report engine, an immune infiltration engine, a microsatellite instability engine, a pathogen infection status engine, a T cell receptor or B cell receptor profiling engine, a line of therapy engine, a metastatic prediction engine, an progression risk prediction engine, and so forth.

An example tumor origin or tumor of unknown origin engine is disclosed, for example, in U.S. patent application Ser. No. 15/930,234, titled "Systems and Methods for Multi-Label Cancer Classification", and filed May 12, 2020, which is incorporated herein by reference and in its entirety for all purposes.

An example of an HLA LOH engine is disclosed, for example, in U.S. Pat. No. 11,081,210, titled "Detection of Human Leukocyte Antigen Class I Loss of Heterozygosity in Solid Tumor Types by NGS DNA Sequencing", and issued Aug. 3, 2021, which is incorporated herein by reference and in its entirety for all purposes. An additional example of an HLA LOH engine is disclosed, for example, in U.S. patent application Ser. No. 17/304,940, titled "Detection of Human Leukocyte Antigen Loss of Heterozygosity", and filed Jun. 28, 2021, which is incorporated herein by reference and in its entirety for all purposes.

An example of a tumor mutational burden (TMB) engine is disclosed, for example, in U.S. Patent Publication No. 2020/0258601, titled "Targeted-Panel Tumor Mutational Burden Calculation Systems and Methods", and published Aug. 13, 2020, which is incorporated herein by reference and in its entirety for all purposes.

An example of a PD-L1 status engine is disclosed, for example, in U.S. Patent Publication No. 2020/0395097, titled "A Pan-Cancer Model to Predict The PD-L1 Status of a Cancer Cell Sample Using RNA Expression Data and Other Patient Data", and published Dec. 17, 2020, which is incorporated herein by reference and in its entirety for all purposes. An additional example of a PD-L1 status engine is disclosed, for example, in U.S. Pat. No. 10,957,041, titled "Determining Biomarkers from Histopathology Slide Images", issued Mar. 23, 2021, which is incorporated herein by reference and in its entirety for all purposes.

An example of a homologous recombination deficiency engine is disclosed, for example, in U.S. Pat. No. 10,975,445, titled "An Integrative Machine-Learning Framework to Predict Homologous Recombination Deficiency", and issued Apr. 13, 2021, which is incorporated herein by reference and in its entirety for all purposes. An additional example of a homologous recombination deficiency engine is disclosed, for example, in U.S. patent application Ser. No. 17/492,518, titled "Systems and Methods for Predicting Homologous Recombination Deficiency Status of a Specimen", filed Oct. 1, 2021, which is incorporated herein by reference and in its entirety for all purposes.

An example of a cellular pathway activation report engine is disclosed, for example, in U.S. Patent Publication No. 2021/0057042, titled "Systems And Methods For Detecting Cellular Pathway Dysregulation In Cancer Specimens", and published Feb. 25, 2021, which is incorporated herein by reference and in its entirety for all purposes.

An example of an immune infiltration engine is disclosed, for example, in U.S. Patent Publication No. 2020/0075169, titled "A Multi-Modal Approach to Predicting Immune Infiltration Based on Integrated RNA Expression and Imaging Features", and published Mar. 5, 2020, which is incorporated herein by reference and in its entirety for all purposes.

An example of an MSI engine is disclosed, for example, in U.S. Patent Publication No. 2020/0118644, titled "Microsatellite Instability Determination System and Related Methods", and published Apr. 16, 2020, which is incorporated herein by reference and in its entirety for all purposes. An additional example of an MSI engine is disclosed, for example, in U.S. Patent Publication No. 2021/0098078, titled "Systems and Methods for Detecting Microsatellite Instability of a Cancer Using a Liquid Biopsy", and published Apr. 1, 2021, which is incorporated herein by reference and in its entirety for all purposes.

An example of a pathogen infection status engine is disclosed, for example, in U.S. Pat. No. 11,043,304, titled "Systems And Methods For Using Sequencing Data For Pathogen Detection", and issued Jun. 22, 2021, which is incorporated herein by reference and in its entirety for all purposes. Another example of a pathogen infection status engine is disclosed, for example, in PCT/US21/18619, titled "Systems And Methods For Detecting Viral DNA From Sequencing", and filed Feb. 18, 2021, which is incorporated herein by reference and in its entirety for all purposes.

An example of a T cell receptor or B cell receptor profiling engine is disclosed, for example, in U.S. patent application Ser. No. 17/302,030, titled "TCR/BCR Profiling Using Enrichment with Pools of Capture Probes", and filed Apr. 21, 2021, which is incorporated herein by reference and in its entirety for all purposes.

An example of a line of therapy engine is disclosed, for example, in U.S. Patent Publication No. 2021/0057071, titled "Unsupervised Learning And Prediction Of Lines Of Therapy From High-Dimensional Longitudinal Medications Data", and published Feb. 25, 2021, which is incorporated herein by reference and in its entirety for all purposes.

An example of a metastatic prediction engine is disclosed, for example, in U.S. Pat. No. 11,145,416, titled "Predicting likelihood and site of metastasis from patient records", and issued Oct. 12, 2021, which is incorporated herein by reference and in its entirety for all purposes.

An example of an 10 progression risk prediction engine is disclosed, for example, in U.S. patent application Ser. No. 17/455,876, titled "Determination of Cytotoxic Gene Signature and Associated Systems and Methods For Response Prediction and Treatment", and filed Nov. 19, 2021, which is incorporated herein by reference and in its entirety for all purposes.

An additional example of a microsatellite instability engine is disclosed, for example, in U.S. patent application Ser. No. 16/412,362, titled "A Generalizable and Interpretable Deep Learning Framework for Predicting MSI From Histopathology Slide Images", and filed May 14, 2019, which is incorporated herein by reference and in its entirety for all purposes.

An example of a radiomics engine is disclosed, for example, in U.S. patent application Ser. No. 16/460,975, titled "3D Radiomic Platform for Imaging Biomarker Development", and filed Jul. 2, 2019, which is incorporated herein by reference and in its entirety for all purposes.

An example of a tissue segmentation engine is disclosed, for example, in U.S. patent application Ser. No. 16/732,242, titled "Artificial Intelligence Segmentation Of Tissue Images", and filed Dec. 31, 2019, which is incorporated herein by reference and in its entirety for all purposes.

When the digital and laboratory health care platform further includes a report generation engine, the methods and systems described above may be utilized to create a summary report of a patient's genetic profile and the results of one or more insight engines for presentation to a physician, including embedding predictions herein (unimodal and multimodal). For instance, the report may provide to the physician information about the extent to which the specimen that was sequenced contained tumor or normal tissue from a first organ, a second organ, a third organ, and so forth. For example, the report may provide a genetic profile for each of the tissue types, tumors, or organs in the specimen, as well the as the embedding predictions. The genetic profile may represent genetic sequences present in the tissue type, tumor, or organ and may include variants, expression levels, information about gene products, or other information that could be derived from genetic analysis of a tissue, tumor, or organ.

The report may include therapies and/or clinical trials matched based on a portion or all of the genetic profile or insight engine findings and summaries, including the based on the embedding predictions. For example, the clinical trials may be matched according to the systems and methods disclosed in U.S. Patent Publication No. 2020/0381087, titled "Systems and Methods of Clinical Trial Evaluation", published Dec. 3, 2020, which is incorporated herein by reference and in its entirety for all purposes.

The report may include a comparison of the results (for example, molecular and/or clinical patient data) to a database of results from many specimens. An example of methods and systems for comparing results to a database of results are disclosed in U.S. Patent Publication No. 2020/0135303 titled "User Interface, System, And Method For Cohort Analysis" and published Apr. 30, 2020, and U.S. Patent Publication No. 2020/0211716 titled "A Method and Process for Predicting and Analyzing Patient Cohort Response, Progression and Survival", and published Jul. 2, 2020, which is incorporated herein by reference and in its entirety for all purposes. The information may be used, sometimes in conjunction with similar information from additional specimens and/or clinical response information, to match therapies likely to be successful in treating a patient, discover biomarkers or design a clinical trial.

Any data generated by the systems and methods and/or the digital and laboratory health care platform may be downloaded by the user. In one example, the data may be downloaded as a CSV file comprising clinical and/or molecular data associated with tests, data structuring, and/or other services ordered by the user. In various embodiments, this may be accomplished by aggregating clinical data in a system backend, and making it available via a portal. This data may include not only variants and RNA expression data, but also data associated with immunotherapy markers such as MSI and TMB, as well as RNA fusions.

When the digital and laboratory health care platform further includes a device comprising a microphone and speaker for receiving audible queries or instructions from a user and delivering answers or other information, the methods and systems described above may be utilized to add data to a database the device can access. An example of such a device is disclosed, for example, in U.S. Patent Publication No. 2020/0335102, titled "Collaborative Artificial Intelligence Method And System", and published Oct. 22, 2020, which is incorporated herein by reference and in its entirety for all purposes.

When the digital and laboratory health care platform further includes a mobile application for ingesting patient records, including genomic sequencing records and/or results even if they were not generated by the same digital and laboratory health care platform, the methods and systems described above may be utilized to receive ingested patient records. An example of such a mobile application is disclosed, for example, in U.S. Pat. No. 10,395,772, titled "Mobile Supplementation, Extraction, And Analysis Of Health Records", and issued Aug. 27, 2019, which is incorporated herein by reference and in its entirety for all purposes. Another example of such a mobile application is disclosed, for example, in U.S. Pat. No. 10,902,952, titled "Mobile Supplementation, Extraction, And Analysis Of Health Records", and issued Jan. 26, 2021, which is incorporated herein by reference and in its entirety for all purposes. Another example of such a mobile application is disclosed, for example, in U.S. Patent Publication No. 2021/0151192, titled "Mobile Supplementation, Extraction, And Analysis Of Health Records", and filed May 20, 2021, which is incorporated herein by reference and in its entirety for all purposes.

When the digital and laboratory health care platform further includes organoids developed in connection with the platform (for example, from the patient specimen), the methods and systems may be used to further evaluate genetic sequencing data derived from an organoid and/or the organoid sensitivity, especially to therapies matched based on a portion or all of the information determined by the systems and methods, including predicted cancer type(s), likely tumor origin(s), etc. These therapies may be tested on the organoid, derivatives of that organoid, and/or similar organoids to determine an organoid's sensitivity to those therapies. Any of the results may be included in a report. If the organoid is associated with a patient specimen, any of the results may be included in a report associated with that patient and/or delivered to the patient or patient's physician or clinician. In various examples, organoids may be cultured and tested according to the systems and methods disclosed in U.S. Patent Publication No. 2021/0155989, titled "Tumor Organoid Culture Compositions, Systems, and Methods", published May 27, 2021; PCT/US20/56930, titled "Systems and Methods for Predicting Therapeutic Sensitivity", filed Oct. 22, 2020; U.S. Patent Publication No. 2021/0172931, titled "Large Scale Organoid Analysis", published Jun. 10, 2021; PCT/US2020/063619, titled "Systems and Methods for High Throughput Drug Screening", filed Dec. 7, 2020 and U.S. patent application Ser. No. 17/301,975, titled "Artificial Fluorescent Image Systems and Methods", filed Apr. 20, 2021 which are each incorporated herein by reference and in their entirety for all purposes. In one example, the drug sensitivity assays may be especially informative if the systems and methods return results that match with a variety of therapies, or multiple results (for example, multiple equally or similarly likely cancer types or tumor origins), each matching with at least one therapy.

When the digital and laboratory health care platform further includes application of one or more of the above in combination with or as part of a medical device or a laboratory developed test that is generally targeted to medical care and research, such laboratory developed test or medical device results may be enhanced and personalized through the use of artificial intelligence. An example of a laboratory developed tests, especially those that may be enhanced by artificial intelligence, is disclosed, for example, in U.S. Patent Publication No. 2021/0118559, titled "Artificial Intelligence Assisted Precision Medicine Enhancements to Standardized Laboratory Diagnostic Testing", and published Apr. 22, 2021, which is incorporated herein by reference and in its entirety for all purposes.

It should be understood that the examples given above are illustrative and do not limit the uses of the systems and methods described herein in combination with a digital and laboratory health care platform.

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components or multiple components.

Additionally, certain embodiments are described herein as including logic or a number of routines, subroutines, applications, or instructions. These may constitute either software (e.g., code embodied on a machine-readable medium or in a transmission signal) or hardware. In hardware, the routines, etc., are tangible units capable of performing certain operations and may be configured or arranged in a certain manner. In example embodiments, one or more computer systems (e.g., a standalone, client or server computer system) or one or more hardware modules of a computer system (e.g., a processor or a group of processors) may be configured by software (e.g., an application or application portion) as a hardware module that operates to perform certain operations as described herein.

In various embodiments, a hardware module may be implemented mechanically or electronically. For example, a hardware module may comprise dedicated circuitry or logic that is permanently configured (e.g., as a special-purpose processor, such as a microcontroller, field programmable gate array (FPGA) or an application-specific integrated circuit (ASIC)) to perform certain operations. A hardware module may also comprise programmable logic or circuitry (e.g., as encompassed within a general-purpose processor or other programmable processor) that is temporarily configured by software to perform certain operations. It will be appreciated that the decision to implement a hardware module mechanically, in dedicated and permanently configured circuitry, or in temporarily configured circuitry (e.g., configured by software) may be driven by cost and time considerations.

Accordingly, the term "hardware module" should be understood to encompass a tangible entity, be that an entity that is physically constructed, permanently configured (e.g., hardwired), or temporarily configured (e.g., programmed) to operate in a certain manner or to perform certain operations described herein. Considering embodiments in which hardware modules are temporarily configured (e.g., programmed), each of the hardware modules need not be configured or instantiated at any one instance in time. For example, where the hardware modules comprise a general-purpose processor configured using software, the general-purpose processor may be configured as respective different hardware modules at different times. Software may accordingly configure a processor, for example, to constitute a particular hardware module at one instance of time and to constitute a different hardware module at a different instance of time.

Hardware modules can provide information to, and receive information from, other hardware modules. Accordingly, the described hardware modules may be regarded as being communicatively coupled. Where multiple of such hardware modules exist contemporaneously, communications may be achieved through signal transmission (e.g., over appropriate circuits and buses) that connects the hardware modules. In embodiments in which multiple hardware modules are configured or instantiated at different times, communications between such hardware modules may be achieved, for example, through the storage and retrieval of information in memory structures to which the multiple hardware modules have access. For example, one hardware module may perform an operation and store the output of that operation in a memory device to which it is communicatively coupled. A further hardware module may then, at a later time, access the memory device to retrieve and process the stored output. Hardware modules may also initiate communications with input or output devices, and can operate on a resource (e.g., a collection of information).

The various operations of the example methods described herein can be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions. The modules referred to herein may, in some example embodiments, comprise processor-implemented modules.

Similarly, the methods or routines described herein may be at least partially processor-implemented. For example, at least some of the operations of a method can be performed by one or more processors or processor-implemented hardware modules. The performance of certain of the operations may be distributed among the one or more processors, not only residing within a single machine, but also deployed across a number of machines. In some example embodiments, the processor or processors may be located in a single location (e.g., within a home environment, an office environment or as a server farm), while in other embodiments the processors may be distributed across a number of locations.

The performance of certain of the operations may be distributed among the one or more processors, not only residing within a single machine, but also deployed across a number of machines. In some example embodiments, the one or more processors or processor-implemented modules may be located in a single geographic location (e.g., within a home environment, an office environment, or a server farm). In other example embodiments, the one or more processors or processor-implemented modules may be distributed across a number of geographic locations.

Unless specifically stated otherwise, discussions herein using words such as "processing," "computing," "calculating," "determining," "presenting," "displaying," or the like may refer to actions or processes of a machine (e.g., a computer) that manipulates or transforms data represented as physical (e.g., electronic, magnetic, or optical) quantities within one or more memories (e.g., volatile memory, non-volatile memory, or a combination thereof), registers, or other machine components that receive, store, transmit, or display information.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

Some embodiments may be described using the expression "coupled" and "connected" along with their derivatives. For example, some embodiments may be described using the term "coupled" to indicate that two or more elements are in direct physical or electrical contact. The term "coupled," however, may also mean that two or more elements are not in direct contact with each other, but yet still co-operate or interact with each other. The embodiments are not limited in this context.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the description. This description, and the claims that follow, should be read to include one or at least one and the singular also includes the plural unless it is obvious that it is meant otherwise.

This detailed description is to be construed as an example only and does not describe every possible embodiment, as describing every possible embodiment would be impractical, if not impossible. One could implement numerous alternate embodiments, using either current technology or technology developed after the filing date of this application.

What is claimed:

1. A computer-implemented method for identifying a multimodal biomarker of a prognostic prediction for a tumor sample, the method comprising:
   a) obtaining, using one or more processors, a radiomic dataset for a tumor sample, the radiomic dataset comprising characteristics of a lesion and/or associated tissue and subsequent analysis and classification of the characteristic corresponding to the tumor sample;
   b) obtaining, using the one or more processors, a pathology dataset for the tumor sample, the pathology dataset comprising characteristics of cells, cell types, cell shapes, and/or cell areas corresponding to the tumor sample;
   c) obtaining, using the one or more processors, a molecular dataset for the tumor sample, the molecular dataset comprising data derived from sequencing data and/or subsequent analysis and classification of the sequencing data corresponding to the tumor sample;
   d) providing, using the more or more processors, the radiomic dataset, the pathology dataset, and the molecular modality dataset to a trained deep learning framework and
   e) generating, using the trained deep learning framework, a radiomic embedding prediction, a pathology embedding prediction, and a molecular embedding prediction; and
   f) applying, using the trained deep learning framework, the radiomic embedding prediction, the pathology embedding prediction, and the molecular embedding prediction to a loss minimization to reduce unimodal embeddings for each prior to an embedding fusion to generate a multimodal embedding prediction as the multimodal biomarker corresponding to the prognostic prediction for the tumor sample,
   wherein the trained deep learning framework comprises a unimodal embeddings layer for generating the radiomic embedding prediction, the pathology embedding prediction, and the molecular embedding prediction and a fully-connected output layer for generating the multimodal embedding prediction, and
   wherein the trained deep learning framework is configured to apply, subsequent to the loss minimization at the unimodal embeddings layer, a second loss function at the fully-connected output layer to generate the multimodal embedding prediction as the multimodal biomarker.

2. The method of claim 1, wherein the radiomic dataset is selected from the group consisting of a magnetic resonance imaging (MRI) image dataset, a computed tomography (CT) image dataset, a fluorescence image dataset, and an x-ray image dataset.

3. The method of claim 1, wherein the pathology dataset is selected from the group consisting of a hematoxylin and eosin (H&E) stained slide image dataset, an immunohistochemistry (IHC) stained slide image dataset, and a fluorescence in situ hybridization (FISH) image dataset.

4. The method of claim 1, wherein the molecular dataset is selected from the group consisting of gene sequencing data, RNA data, DNA data, methylation data, and proteomic data.

5. The method of claim 1, wherein generating, using the trained deep learning framework, the radiomic embedding prediction, the pathology embedding prediction, and the molecular embedding prediction comprises:
  i) feeding, within the trained deep learning framework, the radiomic dataset to a radiomic neural network trained to generate the radiomic embedding prediction;
  ii) feeding, within the trained deep learning framework, the pathology dataset to a pathology neural network trained to generate the pathology embedding prediction; and
  iii) feeding, within the trained deep learning framework, the molecular dataset to a molecular neural network trained to generate the molecular embedding prediction.

6. The method of claim 5, wherein the radiomic neural network is a convolutional neural network.

7. The method of claim 6, wherein the convolutional neural network has been trained using multiparametric MRI training images and labeled image features.

8. The method of claim 7, wherein the convolutional neural network comprises a T1 trained convolutional neural network branch, a T2 trained convolutional neural network branch, and a labeled image features branch.

9. The method of claim 5, wherein the pathology neural network is a convolutional neural network.

10. The method of claim 5, wherein the molecular neural network is a self-normalizing neural network.

11. The method of claim 1, wherein the trained deep learning framework is configured to apply, as the loss minimization, a unimodal loss minimization for the unimodal embeddings layer.

12. The method of claim 1, wherein the trained deep learning framework is configured to apply, as the loss minimization, a multimodal orthogonalization loss across each of the radiomic embedding prediction, the pathology embedding prediction, and the molecular embedding prediction.

13. The method of claim 1, further comprising:
  e) performing, using the trained deep learning framework, a multimodal fusion on the radiomic embedding prediction, the pathology embedding prediction, and the molecular embedding prediction;
  f) generating a multidimensional fusion matrix containing a plurality of multidimensional embeddings, containing at least one or more bi-modal embeddings or one or more tri-modal embeddings; and
  g) determining the multimodal embedding prediction from a comparison of the plurality of multidimensional embeddings.

14. The method of claim 1, further comprising
  h) generating the multimodal embedding prediction is a prediction of overall survival rate corresponding to the tumor sample.

15. The method of claim 1, further comprising
  i) generating the multimodal embedding prediction by:
    A) generating a plurality of multimodal embeddings each having a prediction score; and
    B) identifying a maximum prediction score as the multimodal embedding prediction.

16. The method of claim 1, further comprising,
  j) using the loss minimization,
  k) applying a multimodal orthogonalization across the radiomic embedding prediction, the pathology embedding prediction, and the molecular embedding prediction.

17. The method of claim 16, further comprising
  l) applying an attention weighting to the radiomic embedding prediction, the pathology embedding prediction, and the molecular embedding prediction and, in response,
  m) performing the embedding fusion to generate the multimodal embedding prediction.

18. The method of claim 1, further comprising:
  n) receiving additional features from the radiomic dataset, the pathology dataset, and/or the molecular dataset, the additional features not being used by the deep learning framework in generating the radiomic embedding prediction, the pathology embedding prediction, and the molecular embedding prediction; and
  o) using, in the trained deep learning framework, the additional features to generate the multimodal embedding prediction.

19. A system for identifying a multimodal biomarker of a prognostic prediction for a tumor sample, the system comprising:
  I) one or more processors; and
  II) a trained deep learning framework application including computing instructions configured to be executed by the one or more processors to;
    A) receive a radiomic image modality dataset for a tumor sample, a pathology image modality dataset for the tumor sample, and a molecular modality dataset for the tumor sample, wherein the radiomic dataset comprises characteristics of a lesion and/or associated tissue and subsequent analysis and classification of the characteristic corresponding to the tumor sample, the pathology dataset comprises characteristics of cells, cell types, cell shapes, and/or cell areas corresponding to the tumor sample, and the molecular dataset comprises data derived from sequencing data and/or subsequent analysis and classification of the sequencing data corresponding to the tumor sample;
    B) generate a radiomic embedding prediction, a pathology embedding prediction, and a molecular embedding prediction; and
    C) from the radiomic embedding prediction, the pathology embedding prediction, and the molecular embedding prediction, applying a loss minimization to reduce unimodal embeddings for each prior to an embedding fusion, generate a multimodal embedding prediction as the multimodal biomarker corresponding to the prognostic prediction for the tumor sample,
  wherein the trained deep learning framework comprises a unimodal embeddings layer for generating the radiomic embedding prediction, the pathology embedding prediction, and the molecular embedding prediction and a fully-connected output layer for generating the multimodal embedding prediction, and
  wherein the trained deep learning framework is configured to apply, subsequent to the loss minimization at the unimodal embeddings layer, a second loss function at the fully-connected output layer to generate the multimodal embedding prediction as the multimodal biomarker.

* * * * *